(12) United States Patent
Maekita et al.

(10) Patent No.: US 10,449,107 B2
(45) Date of Patent: Oct. 22, 2019

(54) GAIT TRAINING APPARATUS

(71) Applicant: TOYOTA JUDOSHA KABUSHIKI KAISHA, Toyota-shi (JP)

(72) Inventors: Tomoe Maekita, Toyota (JP); Hiroshi Shimada, Tajimi (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 126 days.

(21) Appl. No.: 15/833,102

(22) Filed: Dec. 6, 2017

(65) Prior Publication Data

US 2018/0161230 A1 Jun. 14, 2018

(30) Foreign Application Priority Data

Dec. 8, 2016 (JP) ................................ 2016-238873

(51) Int. Cl.
*A61H 3/00* (2006.01)
*A61H 1/02* (2006.01)
(Continued)

(52) U.S. Cl.
CPC .............. *A61H 3/008* (2013.01); *A61B 5/112* (2013.01); *A61B 5/4836* (2013.01); *A61H 1/02* (2013.01);
(Continued)

(58) Field of Classification Search
CPC ..... A61B 5/002; A61B 5/1038; A61B 5/1117; A61B 5/112; A61B 5/4836;
(Continued)

(56) References Cited

U.S. PATENT DOCUMENTS 5,667,461 A * 9/1997 Hall ..................... A61H 1/0229
472/15
6,126,575 A * 10/2000 Wang ................. A63B 22/0257
482/51
(Continued)

FOREIGN PATENT DOCUMENTS

JP 2010-110543 5/2010
JP 2015-223294 12/2015
(Continued)

OTHER PUBLICATIONS

U.S. Appl. No. 15/682,598, filed Aug. 22, 2017, Tomoe Maekita (publication date not available, submitting filed of application), 24 pages.

*Primary Examiner* — Joshua Lee
(74) *Attorney, Agent, or Firm* — Oblon, McClelland, Maier & Neustadt, L.L.P.

(57) ABSTRACT

A gait training apparatus includes a wire configured to directly or indirectly pull a trainee's leg fitted with a gait assist device from a position above the trainee's head; a control unit configured to control a motor that applies a pulling force to the wire, thereby adjusting the pulling force; and a housing mechanism configured to retract or release the wire in response to a motion of the leg. The control unit controls the motor such that the pulling force is adjusted to a predetermined pulling force that is independent of the speed, when a speed at which the housing mechanism retracts or releases the wire is within a prescribed range defined in advance and including zero. The control unit controls the motor such that the pulling force is adjusted to a pulling force calculated based on the speed, when the speed is out of the prescribed range.

14 Claims, 15 Drawing Sheets

(51) Int. Cl.
*A61B 5/11* (2006.01)
*A63B 22/02* (2006.01)
*A61B 5/00* (2006.01)
*A61B 5/103* (2006.01)

(52) U.S. Cl.
CPC ............ *A61H 1/0262* (2013.01); *A61H 3/00* (2013.01); *A63B 22/02* (2013.01); *A61B 5/002* (2013.01); *A61B 5/1038* (2013.01); *A61B 5/1117* (2013.01); *A61B 2505/09* (2013.01); *A61H 2201/1215* (2013.01); *A61H 2201/164* (2013.01); *A61H 2201/5061* (2013.01)

(58) Field of Classification Search
CPC .... A61B 2505/09; A61H 1/02; A61H 1/0262; A61H 3/00; A61H 3/008; A61H 2201/1215; A61H 2201/164; A61H 2201/5061; A63B 22/02
See application file for complete search history.

(56) References Cited

U.S. PATENT DOCUMENTS

| | | | | |
|---|---|---|---|---|
| 7,857,779 B2* | 12/2010 | Gondringer | ............... | A61F 5/04 128/878 |
| 7,887,471 B2* | 2/2011 | McSorley | .......... | A63B 21/0552 482/136 |
| 9,387,384 B2* | 7/2016 | Mehr | ................. | A63B 69/0064 |
| 10,292,892 B2* | 5/2019 | Lee | ........... | A61H 3/00 |
| 2005/0101448 A1* | 5/2005 | He | ...................... | A61H 1/0237 482/54 |
| 2011/0071442 A1* | 3/2011 | Park | ...................... | A61H 1/0262 601/35 |
| 2013/0137553 A1* | 5/2013 | Kim | ...................... | A61H 1/024 482/69 |
| 2014/0058299 A1 | 2/2014 | Sankai et al. | | |
| 2014/0315689 A1* | 10/2014 | Vauquelin | ............. | A63B 69/00 482/8 |
| 2015/0342820 A1* | 12/2015 | Shimada | ............ | A63B 22/0046 482/69 |
| 2017/0027803 A1* | 2/2017 | Agrawal | ............ | A61B 5/6828 |
| 2017/0035642 A1 | 2/2017 | Sugata | | |
| 2017/0049660 A1 | 2/2017 | Sugata | | |
| 2017/0071813 A1 | 3/2017 | Sugata | | |

FOREIGN PATENT DOCUMENTS

| | | |
|---|---|---|
| JP | 2017-35220 | 2/2017 |
| JP | 2017-38658 | 2/2017 |
| JP | 2017-51464 | 3/2017 |
| WO | WO 2012/118143 A1 | 7/2012 |

* cited by examiner

GAIT TRAINING APPARATUS

INCORPORATION BY REFERENCE

The disclosure of Japanese Patent Application No. 2016-238873 filed on Dec. 8, 2016 including the specification, drawings and abstract is incorporated herein by reference in its entirety.

BACKGROUND

1. Technical Field

The disclosure relates to a gait training apparatus.

2. Description of Related Art

Examples of apparatuses that help persons having a difficulty in walking improve their ability to walk include a gait training apparatus equipped with a treadmill. The treadmill includes a rotary belt. A trainee walks on the rotary belt at a speed corresponding to the speed of rotation of the rotary belt, thereby carrying out training. In an early stage of this training, a gait assist device is fitted to the trainee's leg to be trained, in order to reduce a walking load on the trainee, in some cases. The gait assist device assists the trainee's leg movement using, for example, a drive force generated by a motor.

The gait assist device has a certain degree of weight because the gait assist device is equipped with a motor and a sensor. Wearing such a heavy device may place a burden on the trainee. In these circumstances, there has been proposed a gait training apparatus that reduces the burden placed on a trainee due to the weight of a gait assist device. In the gait training apparatus, a winding-up mechanism provided in the vicinity of an area over the head of a trainee pulls up a wire secured to the gait assist device in accordance with the leg movement of the trainee, thereby reducing the burden on the trainee. For example, Japanese Patent Application Publication No. 2015-223294 describes the gait training apparatus.

SUMMARY

There is an apparatus in which a gait assist device is suspended by a wire, and the wire is wound up to be retracted or unwound to be released by a winding-up mechanism to bear the weight of the gait assist device. It has been revealed that, when such an apparatus is used, hunting, that is, a phenomenon in which a weight-bearing force significantly oscillates within a short period of time, occurs in response to a specific movement of a trainee's affected leg to which the gait assist device is fitted.

The disclosure provides a gait training apparatus configured to reduce the occurrence of hunting of a weight-bearing force.

A gait training apparatus according to a first aspect of the disclosure includes a gait assist device fitted to a leg of a trainee and configured to assist a movement of the leg of the trainee. The gait training apparatus includes: a wire configured to directly or indirectly pull the leg fitted with the gait assist device from a position above the trainee's head; a motor configured to apply a pulling force to the wire; a control unit configured to control the motor to adjust the pulling force; a housing mechanism configured to retract or release the wire in response to a motion of the leg; and a speed detecting unit configured to detect a speed at which the housing mechanism retracts or releases the wire. The control unit is configured to control the motor such that the pulling force is adjusted to a predetermined pulling force that is independent of the speed, when the speed is within a prescribed range defined in advance and including zero. The control unit is configured to control the motor such that the pulling force is adjusted to a pulling force calculated based on the speed, when the speed is out of the prescribed range.

With the gait training apparatus configured as described above, the wire is pulled with a pulling force that is independent of the speed at which the wire is retracted or released, in a period that includes the time when the motion of a trainee's affected leg is stopped and in which hunting of the weight-bearing force is likely to occur. Therefore, it is possible to reduce the occurrence of hunting. In periods other than the above-described period, the wire is pulled with a pulling force based on the speed at which the wire is retracted or released. Therefore, it is expected that the influence of a dynamic friction and a viscous friction is cancelled out to provide a certain magnitude of weight-bearing force.

A gait training apparatus according to a second aspect of the disclosure includes a gait assist device fitted to a leg of a trainee and configured to assist a movement of the leg of the trainee. The gait training apparatus includes: a wire configured to directly or indirectly pull the leg fitted with the gait assist device from a position above the trainee's head; a motor configured to apply a pulling force to the wire; a control unit configured to control the motor to adjust the pulling force; a housing mechanism configured to retract or release the wire in response to a motion of the leg; a speed detecting unit configured to detect a speed at which the housing mechanism retracts or releases the wire; and a state detecting unit configured to detect a grounding state of the leg of the trainee. The control unit is configured to control the motor such that the pulling force is adjusted to a predetermined pulling force that is independent of the speed, when the control unit determines, based on a result of detection by the state detecting unit, that the leg is shifted from a swing phase to a stance phase or that the leg is shifted from the stance phase to the swing phase. The control unit is configured to control the motor such that the pulling force is adjusted to a pulling force that is calculated based on the speed, when the control unit determines, based on a result of detection by the state detecting unit, that the leg is maintained in the swing phase or maintained in the stance phase.

With the gait training apparatus configured as described above, the wire is pulled with a pulling force that is independent of the speed at which the wire is retracted or released, in a transient period in which the affected leg is shifted from the swing phase to the stance phase or shifted from the stance phase to the swing phase and hunting of the weight-bearing force is likely to occur. Therefore, it is possible to reduce the occurrence of hunting. In periods other than the above-described period, the wire is pulled with a pulling force based on the speed at which the wire is retracted or released. Therefore, it is expected that the influence of a dynamic friction and a viscous friction is cancelled out to provide a certain magnitude of weight-bearing force.

According to the disclosure, it is possible to provide a gait training apparatus that curbs the occurrence of hunting of weight-bearing force.

BRIEF DESCRIPTION OF THE DRAWINGS

Features, advantages, and technical and industrial significance of exemplary embodiments will be described below with reference to the accompanying drawings, in which like numerals denote like elements, and wherein.

DETAILED DESCRIPTION OF EMBODIMENTS

Hereinafter, the disclosure will be described based on the following embodiments. However, the following embodiments are not intended to limit the disclosure. Moreover, it is not absolutely necessary to provide all the configurations to be described in the following embodiments.

Figure 1:
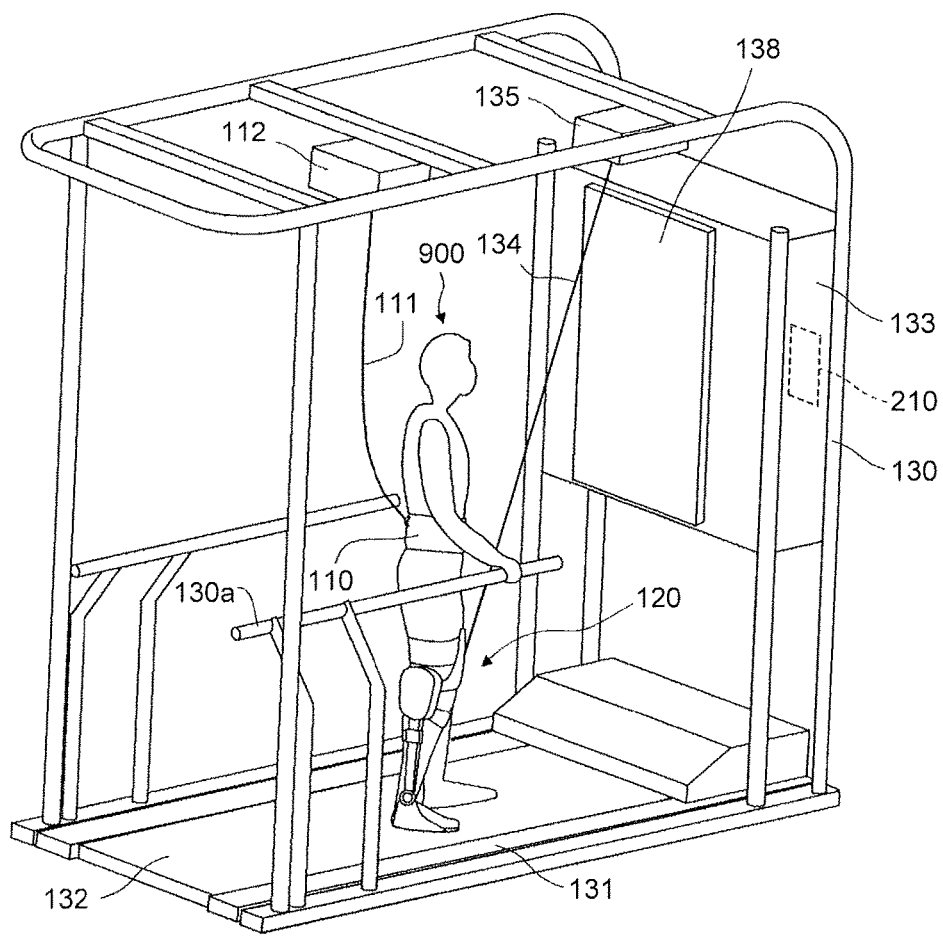
FIG. 1 is a schematic perspective view of a gait training apparatus according to an embodiment.

FIG. 1 is a schematic perspective view of a gait training apparatus 100 according to a present embodiment. The gait training apparatus 100 is an apparatus for a trainee 900, for example, a disabled person with a disability, such as hemiplegia, or an elderly person who has lost strength in his/her leg, to carry out gait training. The gait training apparatus 100 mainly includes a support pulling unit 135 and harness pulling unit 112 that are attached to a frame 130, which constitutes an overall framework, a treadmill 131 on which the trainee 900 walks, and a gait assist device 120 fitted to a leg of the trainee 900.

The frame 130 is set up on the treadmill 131 disposed on a floor. The treadmill 131 includes a belt 132 having a ring-shape and rotated by a motor (not illustrated) configured to rotate the belt 132. The treadmill 131 is a device that prompts the trainee 900 to walk. The trainee 900 who carries out gait training gets on the belt 132 and tries a walking action in accordance with the movement of the belt 132.

The frame 130 supports, for example, a control board 133 that houses an overall control unit 210 configured to control a motor and a sensor, and a display unit 138, such as a liquid crystal panel, configured to display, for example, a progress status of the training. The frame 130 supports the support pulling unit 135 in the vicinity of an area above and ahead of the head of the trainee 900, and supports the harness pulling unit 112 in the vicinity of an area over the head of the trainee 900. The frame 130 includes handrails 130a that the trainee 900 holds.

The support wire 134 is coupled at one end to a winding-up mechanism of the support pulling unit 135, and is coupled at the other end to the gait assist device 120. The winding-up mechanism of the support pulling unit 135 is configured to wind up or unwind the support wire 134 in response to the movement of an affected leg of the trainee 900, by adjusting an output of a motor (not illustrated).

The gait training apparatus 100 includes a fall-prevention harness device serving as a safety device and including a harness 110, a harness wire 111, and the harness pulling unit 112. The harness 110 is a belt to be wounded around the waist of the trainee 900 and to be secured to the waist of the trainee 900 through, for example, a hook-and-loop fastener. The harness 110 includes a coupling hook 110a to which one end of the harness wire 111, which is a hanging tool, is coupled. The trainee 900 wears the harness 110 such that the coupling hook 110a is positioned on his/her lower back.

The harness wire 111 is coupled at the one end to the coupling hook 110a of the harness 110, and is coupled at the other end to the winding-up mechanism of the harness pulling unit 112. The winding-up mechanism of the harness pulling unit 112 is configured to wind up or unwind the harness wire 111 by adjusting an output of a motor (not illustrated). With this configuration, when the trainee 900 is about to fall, the fall-prevention harness device winds up the harness wire 111 according to an instruction from the overall control unit 210 that detects such a movement of the trainee 900, thereby supporting the upper body of the trainee 900 to prevent the trainee 900 from falling.

Figure 2:
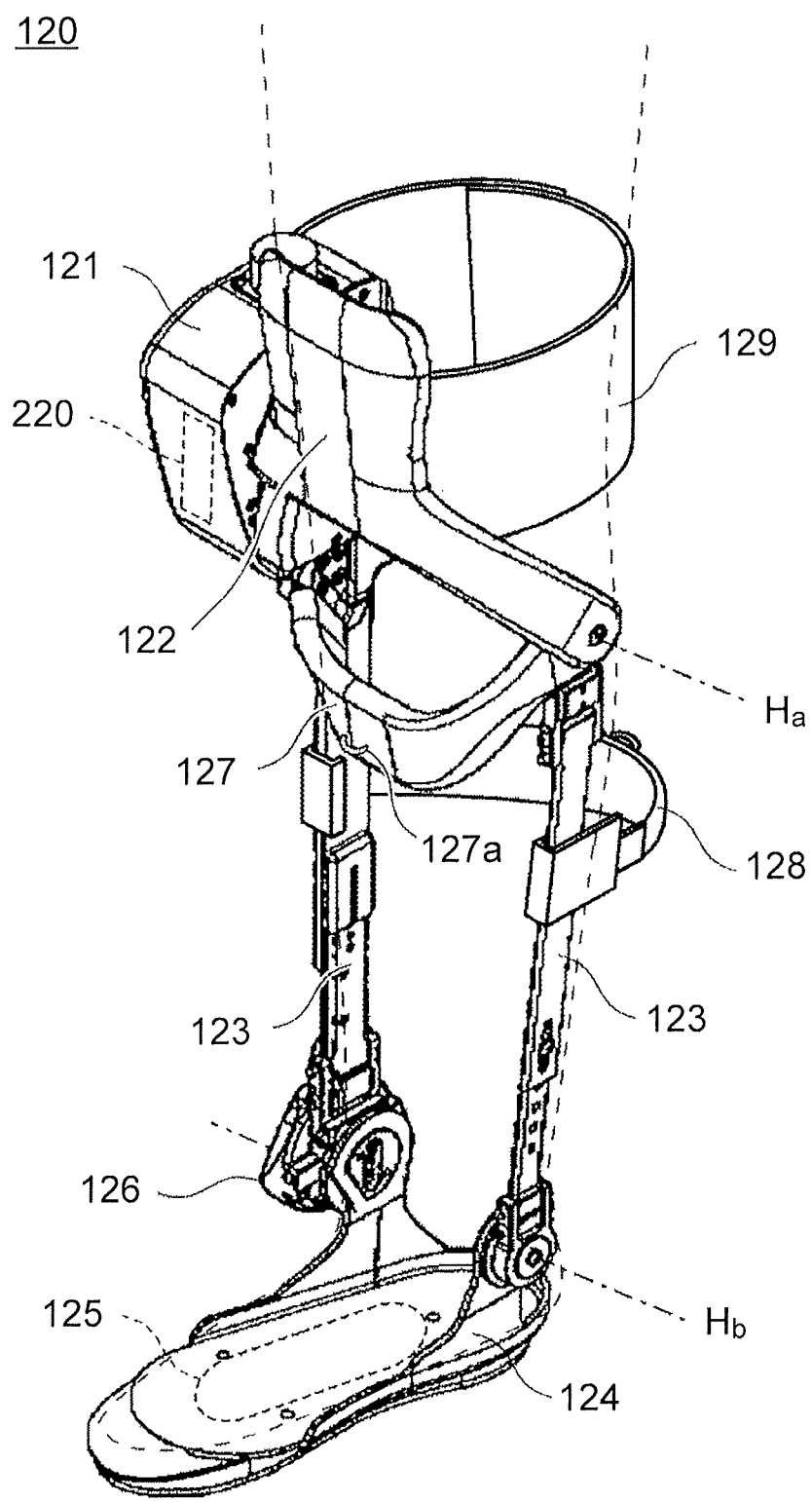
FIG. 2 is a schematic perspective view of a gait assist device.

The gait assist device 120 is fitted to the affected leg of the trainee 900, that is, a leg to be trained. The gait assist device 120 assists the trainee 900 in walking, by reducing a load on the affected leg. The gait assist device 120 includes a sole sensor 125 configured to detect a load applied to the sole of the trainee 900. FIG. 2 is a schematic perspective view of the gait assist device 120. The gait assist device 120 mainly includes a control unit 121 and a plurality of frames configured to support various parts of the affected leg, in addition to the sole sensor 125.

The control unit 121 includes an assist control unit 220 configured to control the gait assist device 120, and further includes a motor (not illustrated) configured to generate a drive force for assisting a flexion movement of the knee joint. The frames configured to support various parts of the affected leg include a thigh frame 122, lower leg frames 123 pivotally coupled to the thigh frame 122, a sole frame 124 pivotally coupled to the lower leg frames 123, a front-side support frame 127 that is configured to support the thigh of the trainee 900 and is coupled to the support wire 134, and a bark-side support frame 128 that is configured to support the calf of the trainee 900.

The thigh frame 122 and the lower leg frames 123 are configured to pivot relative to each other about a hinge axis $H_a$ illustrated in FIG. 2. The motor of the control unit 121 is configured to rotate according to an instruction from the assist control unit 220 to apply a drive force such that the thigh frame 122 and the lower leg frames 123 pivot relative to each other about the hinge axis $H_a$ to increase or decrease the angle therebetween. The lower leg frames 123 and the sole frame 124 are configured to pivot relative to each other about a hinge axis $H_b$ illustrated in FIG. 2. The angle by which the thigh frame 122 and the lower leg frames 123 can pivot relative to each other is adjusted by an adjusting mechanism 126 before the gait training.

The front-side support frame 127 is provided so as to extend in the lateral direction at a position in front of the thigh and to be connected at both ends to the thigh frame 122. The front-side support frame 127 is provided with a coupling hook 127a to which the support wire 134 is coupled. The coupling hook 127a is provided in the vicinity of the center of the front-side support frame 127 in the lateral direction. The bark-side support frame 128 is provided so as to extend in the lateral direction at a position behind the lower leg and to be connected at both ends to the lower leg frames 123 extending in the up-down direction.

The thigh frame 122 includes a thigh belt 129. The thigh belt 129 is a belt that is integrated with the thigh frame 122. The thigh belt 129 is wound around the thigh of the affected leg to secure the thigh frame 122 to the thigh. This configuration reduces the displacement of the entirety of the gait assist device 120 from the leg of the trainee 900.

The sole sensor 125 is a load sensor that is embedded in the sole frame 124. The sole sensor 125 is configured to detect a magnitude and a distribution of a vertical load received by the sole of the trainee 900. The sole sensor 125 is, for example, a resistance-variation-detection-type load detecting sheet including electrodes arranged in a matrix pattern.

Figure 3:
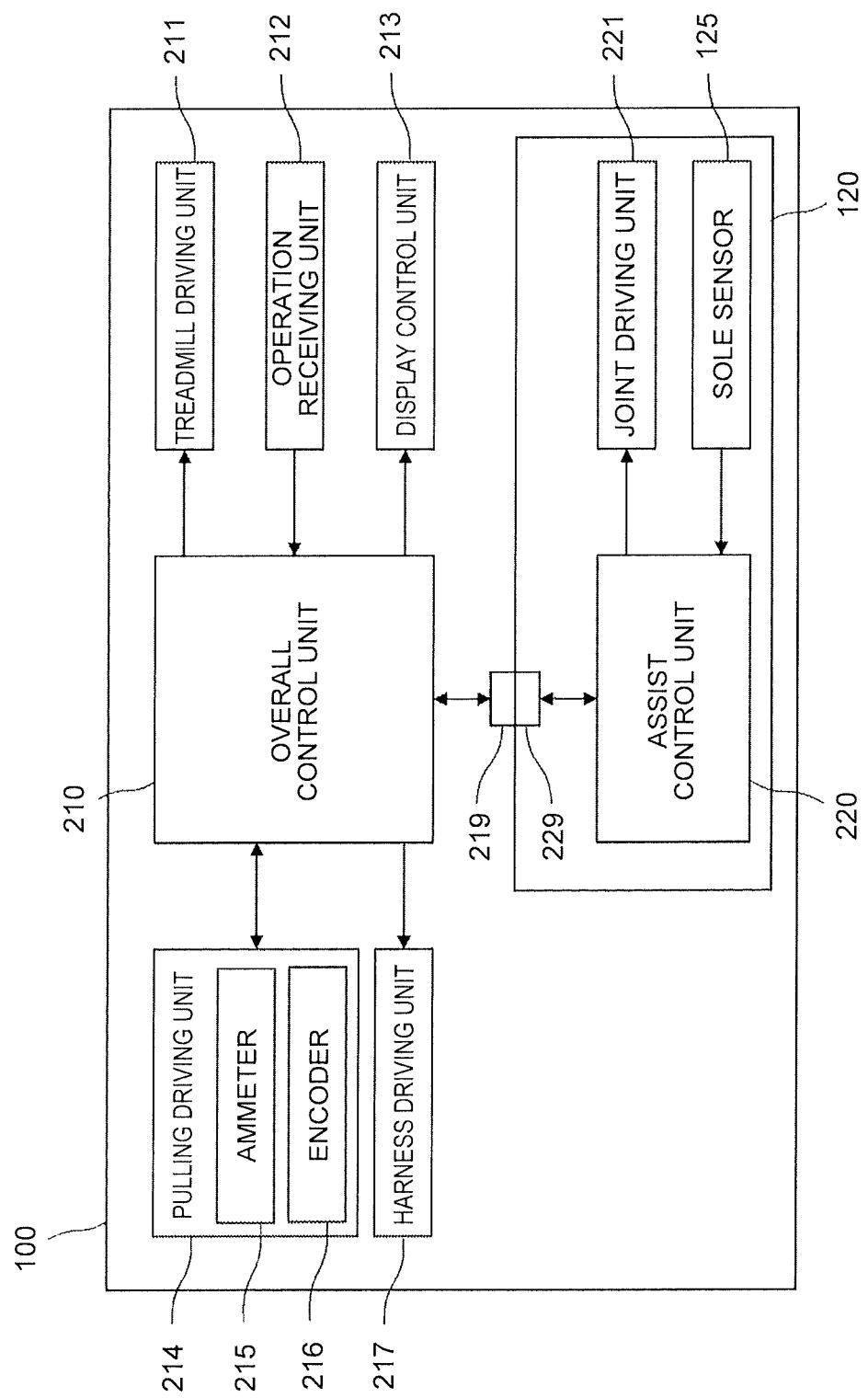
FIG. 3 is a diagram illustrating the system configuration of the gait training apparatus.

Next, the system configuration of the gait training apparatus 100 will be described. FIG. 3 is a system configuration diagram of the gait training apparatus 100. The overall control unit 210 is, for example, a central processing unit (CPU). The overall control unit 210 is configured to control the entirety of the gait training apparatus by executing control programs read from a system memory. A treadmill driving unit 211 includes a motor that rotates the belt 132 and a driving circuit for the motor. The overall control unit 210 is configured to transmit a drive signal to the treadmill driving unit 211 to control the rotation of the belt 132. For example, the overall control unit 210 adjusts the rotation speed of the belt 132 according to a walking speed set in advance.

An operation receiving unit 212 is configured to transmit an operation signal to the overall control unit 210 upon reception of an input operation from the trainee 900 or an operator. The trainee 900 or the operator operates operating buttons, a touch panel, an accompanying remote control and the like, which constitute the operation receiving unit 212 and are provided in the gait training apparatus, to turn on or off a power source, issue an instruction to start the training, input a numeric value relating to a setting, or select a menu item.

A display control unit 213 is configured to create a display screen upon reception of a display signal from the overall control unit 210, and to display the display screen on the display unit 138. According to the display signal, the display control unit 213 creates a screen indicating progress of the training or the like.

A pulling driving unit 214 includes a motor for pulling the support wire 134 and a driving circuit for the motor. The motor and the driving circuit constitute the support pulling unit 135. The motor may be, for example, a three-phase induction motor or a stepping motor because the rotation speed and the torque can be easily controlled. The pulling driving unit 214 further includes an ammeter 215 that is built in the driving circuit for the motor and configured to monitor a current flowing into the motor, and an encoder 216 that is provided on a winding shaft of the winding-up mechanism and configured to detect a rotation angle of the winding shaft.

The overall control unit 210 is configured to transmit a drive signal to the pulling driving unit 214 to control winding-up and unwinding of the support wire 134, and control a pulling force to be applied to the support wire 134 at the time of winding-up or unwinding thereof. Specifically, the overall control unit 210 monitors an output from the ammeter 215 to control the amount of electricity to be applied to the motor, thereby adjusting the torque output from the motor. That is, the overall control unit 210 has a function as a control unit configured to adjust the pulling force to be applied to the support wire 134, in cooperation with the ammeter 215. The overall control unit 210 controls the pulling force to be applied to the support wire 134 based on the torque output from the motor without directly measuring a tension of the support wire 134. The overall control unit 210 monitors a detection signal from the encoder 216 to acquire a winding-up amount and a winding speed of the support wire 134. The control will be described later in more detail.

A harness driving unit 217 includes a motor for pulling the harness wire 111 and a driving circuit for the motor. The motor and the driving circuit constitute the harness pulling unit 112. The overall control unit 210 is configured to transmit a drive signal to the harness driving unit 217 to control winding-up of the harness wire 111 and a pulling force of the harness wire 111.

The gait assist device 120 is fitted to the affected leg of the trainee 900 as described above, and the gait training apparatus 100 includes a communication connection IF 219 that is connected to the overall control unit 210 in order to provide an instruction to the gait assist device 120 and receive sensor information. The gait assist device 120 includes a communication connection IF 229 that is connected to the communication connection IF 219 by wire or wirelessly. The communication connection IF 229 is connected to the assist control unit 220 of the gait assist device 120. The communication connection IFs 219, 229 are communication interface conforming to a telecommunications standard, such as the wireless LAN.

The assist control unit 220 is, for example, a central processing unit (CPU). The assist control unit 220 is configured to control the gait assist device 120 by executing control programs provided from the overall control unit 210. The assist control unit 220 is configured to notify the overall control unit 210 of a state of the gait assist device 120, via the communication connection IFs 219, 229. The assist control unit 220 is configured to, for example, start or stop the gait assist device 120 upon reception of an instruction from the overall control unit 210.

A joint driving unit 221 includes the motor of the control unit 121 and a driving circuit for the motor. The assist control unit 220 is configured to transmit a drive signal to the joint driving unit 221 such that the thigh frame 122 and the lower leg frames 123 pivot relative to each other about the hinge axis $H_a$ to increase or decrease the angle therebetween. The sole sensor 125 is configured to detect a magnitude and a distribution of a vertical load received by the sole of the trainee 900 as described above, and to transmit a detection signal to the assist control unit 220. The assist control unit 220 receives and analyzes the detection signal to determine the state of the affected leg of the trainee 900, for example, determine whether the affected leg is in a swing phase or in a stance phase.

Figure 4:
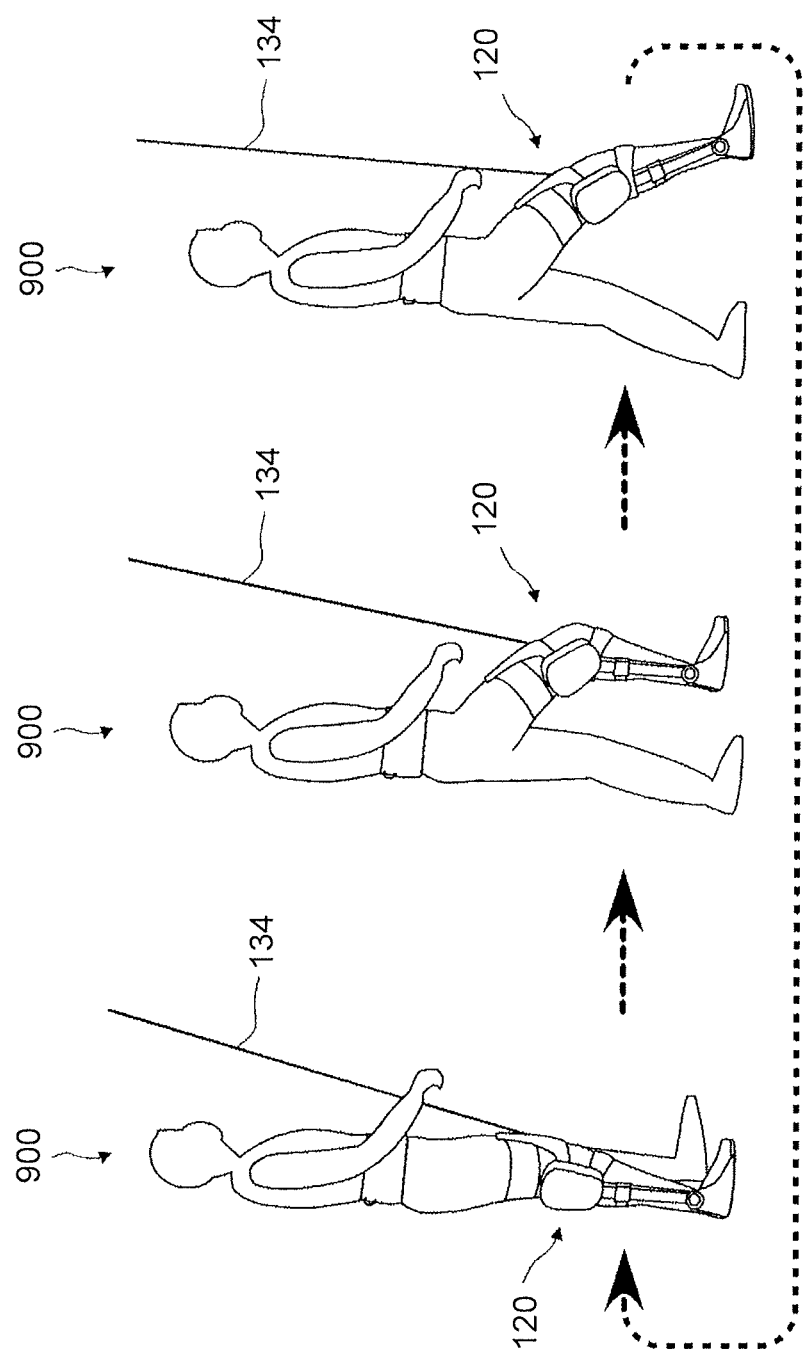
FIG. 4 is a view illustrating how gait training is carried out.

FIG. 4 is a diagram illustrating how the gait training is carried out. FIG. 4 illustrates particularly the relationship between the leg movement of the affected leg and the support wire 134. The trainee 900 is assumed to hold the handrail 130a with his/her right hand.

The left view in FIG. 4 illustrates a foot-grounded state where the affected leg of the trainee 900 is standing substantially upright. In this state, the right leg of the trainee 900, which is the affected leg, is positioned slightly backward of the left leg, and the trainee 900 is about to lift the right leg. The support pulling unit 135 is disposed at a position in front of an area over the head of the trainee 900 as described above, and thus the support wire 134 is unwound to the maximum level from the winding-up mechanism in this state.

The middle view in FIG. 4 illustrates a foot-swinging state where the trainee 900 has lifted the right leg, which is the affected leg, so that the knee of the trainee 900 is at the highest possible position. The swing phase in which the affected leg is lifted is a phase in which the affected leg is moved from the back side to the front side relative to the left leg, which is the pivot leg. In this phase, the support wire 134 is gradually wound up by the winding-up mechanism and retracted in the support pulling unit 135.

The right view in FIG. 4 illustrates a state where the swing phase has ended and the trainee 900 has stepped forward with his/her right leg, which is the affected leg, and grounded his/her right leg. That is, the right view in FIG. 4 illustrates the state immediately after the affected leg is shifted to the foot-grounded state. At this time, the gait assist device 120 and the support pulling unit 135 come closest to each other, and the support wire 134 is wound up to the maximum level by the winding-up mechanism in this state.

Then, the trainee 900 moves the left leg forward while keeping the right leg, which is the affected leg, in the foot-grounded state, so that the state illustrated in the left view in FIG. 4 is achieved again. While the trainee 900 is carrying out such gait training, the belt 132 of the treadmill 131 rotates at a predetermined speed. Thus, the right leg in the foot-grounded state is moved backward while the left leg is moved forward. In this period, the support wire 134 is gradually unwound from the winding-up mechanism. That is, the trainee 900 repeats the walking action on substantially the same spot.

In the gait training apparatus 100 in the present embodiment, the support pulling unit 135 serving as a housing mechanism is disposed at a position above the head of the trainee 900 and ahead of an area on which the affected leg of the trainee 900 is expected to be grounded. Because the support pulling unit 135 is disposed at such a position, the support wire 134 is unwound to the maximum level from the winding-up mechanism in the state illustrated in the left view in FIG. 4 where the affected leg is about to be shifted from the foot-grounded state to the foot-swinging state, and the support wire 134 is wound up to the maximum level by the winding-up mechanism in the state illustrated in the right view in FIG. 4 where the affected leg has been shifted from the foot-swinging state to the foot-grounded state. The support pulling unit 135 can fulfill its function when the support pulling unit 135 is provided at a position above the trainee 900. When the support pulling unit 135 is disposed at the above-described position, the relationship between the leg movement and the support wire 134 is simplified, which facilitates the control described later.

Hereafter, description will be provided on a case where the affected leg is moved relatively smoothly, by way of example, unless otherwise noted. That is, description will be provided on a case where the states illustrated in FIG. 4 make a smooth transition along arrowed dotted lines.

Figure 5:
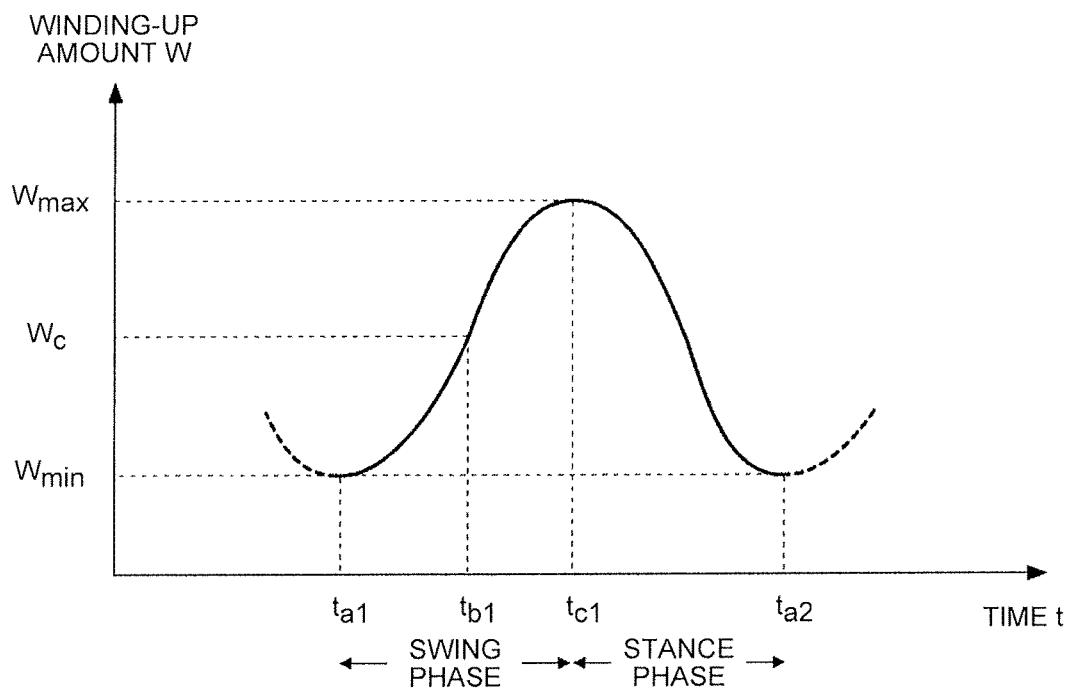
FIG. 5 is a graph illustrating the relationship between the leg movement of a trainee and the winding-up amount of a support wire.

FIG. 5 is a graph illustrating the relationship between the leg movement of the trainee 900 and the winding-up amount of the support wire 134. The abscissa axis of the graph represents the lapse of time, and the ordinate axis of the graph represents the winding-up amount of the support wire 134, that is, the amount by which the support wire 134 is wound up by the winding-up mechanism. A winding-up amount W is a length by which the support wire 134 is wound up by the winding-up mechanism, and is substantially equal to a retracted amount of the support wire 134, which is a length of the support wire 134 retracted in the support pulling unit 135. A curve indicated by a solid line represents one gait cycle corresponding to one step of the affected leg.

At time $t_{a1}$, the trainee 900 is in the state illustrated in the left view in FIG. 4. At this time, the winding-up amount W of the support wire 134, that is, the amount by which the support wire 134 is wound up by the winding-up mechanism, takes a minimum value $W_{min}$. When the trainee 900 lifts the affected leg, the affected leg enters the swing phase. Then, the affected leg undergoes the state illustrated in the middle view in FIG. 4 at time $t_{b1}$ (the winding-up amount at this time is $W_c$), and then enters the foot-grounded state illustrated in the right view in FIG. 4 at time $t_{c1}$, so that the swing phase ends. At time $t_{b1}$, the winding-up amount W of the support wire 134, that is, the amount by which the support wire 134 is wound up by the winding-up mechanism, takes a maximum value $W_{max}$. The affected leg enters the stance phase at time $t_{c1}$, and then returns to the state illustrated in the left view in FIG. 4 again at time $t_{a2}$, so that the stance phase ends. The affected leg is returned to the original position in the stance phase, by the action of the treadmill 131. The overall control unit 210 acquires the winding-up amount W by integrating detection signals received from the encoder 216.

Figure 6:
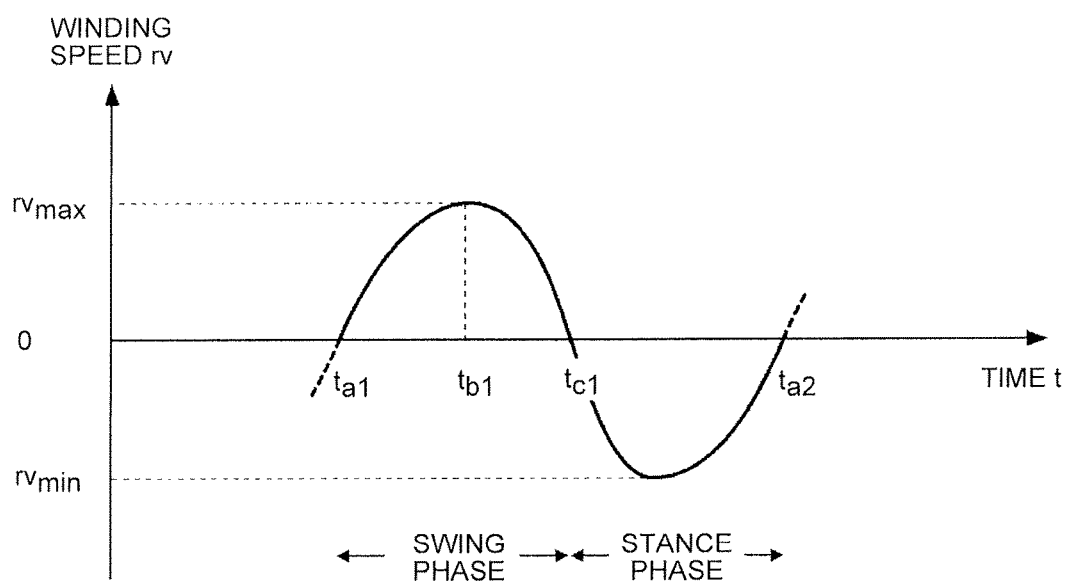
FIG. 6 is a graph illustrating the relationship between the leg movement of the trainee and the winding speed of the support wire.

FIG. 6 is a graph illustrating the relationship between the leg movement of the trainee 900 and the winding speed of the support wire 134. The abscissa axis of the graph represents the lapse of time, and the ordinate axis of the graph represents the winding speed at which the winding-up mechanism winds up the support wire 134. A winding speed rv is a length by which the winding-up mechanism winds up the support wire 134 per unit time. A curve illustrated by a solid line represents one gait cycle corresponding to one step of the affected leg.

At time $t_{a1}$, the trainee 900 is in the state illustrated in the left view in FIG. 4 where the affected leg is at a standstill for a moment. Therefore, the winding speed rv is zero at this time. When the trainee 900 lifts the affected leg, the affected leg enters the swing phase. Until the affected leg enters the state illustrated in the middle view in FIG. 4 at time $t_{b1}$, the winding speed rv gradually increases, and then the winding speed rv reaches a maximum value $rv_{max}$ at time $t_{b1}$. While the leg movement is further continued, the winding speed rv gradually decreases, and the winding speed rv reaches zero again at time $t_{c1}$ at which the affected leg enters the foot-grounded state illustrated in the right view in FIG. 4. During the swing phase, the winding speed rv takes a positive value because the winding-up mechanism winds up the support wire 134.

At time $t_{c1}$, the affected leg enters the stance phase in which the winding speed rv gradually decreases, then reaches a minimum value $rv_{min}$, and then starts increasing. At time $t_{a2}$, the stance phase ends, and the winding speed rv returns to zero again. In the stance phase, the affected leg is moved away from the winding-up mechanism by action of the treadmill 131, so that the support wire 134 is pulled by the gait assist device 120 and unwound, and the winding speed rv takes a negative value. The overall control unit 210 acquires a winding speed rv by receiving detection signals from the encoder 216 and calculating an angular variation per unit time. At this time, the encoder 216 and the overall control unit 210 cooperate with each other to function as a speed detecting unit configured to detect a speed at which the support pulling unit 135 retracts (winds up) or releases (unwinds) the support wire 134.

FIGS. 7A to 7D are diagrams illustrating the relationship between the motion of the support wire 134 and the frictional force. In particular, FIGS. 7A to 7D are enlarged views illustrating the vicinity of the encoder 216 for each action of the support wire 134 and the winding-up mechanism.

The support pulling unit 135 retracts and releases the support wire 134 in accordance with the leg movement of the trainee 900. The main object of this is to bear the weight of the gait assist device 120 that is a burden on the trainee 900 who is carrying out the gait training. That is, the support pulling unit 135 pulls the support wire 134 secured to the gait assist device 120, so as to bear the weight of the gait assist device 120. The support pulling unit 135 can bear a part of the weight of the trainee 900 by pulling the support wire 134 by an amount larger than an amount required to bear the weight of the gait assist device 120. In the present embodiment, however, description will be provided on the assumption that only the weight of the gait assist device 120 is borne.

When the trainee 900 is lifting the affected leg, the winding-up mechanism winds up the support wire 134 by a surplus length. When the affected leg is moved away from the winding-up mechanism in the stance phase, the winding-up mechanism unwinds the support wire 134 by a length by which the support wire 134 is pulled by the affected leg. In each of a case where the winding-up mechanism winds up the support wire 134 and a case where the winding-up mechanism unwinds the support wire 134, the motor (not illustrated) applies torque to the winding shaft of the winding-up mechanism, thereby applying a pulling force corresponding to the weight of the gait assist device 120, to the support wire 134.

Figure 7A:
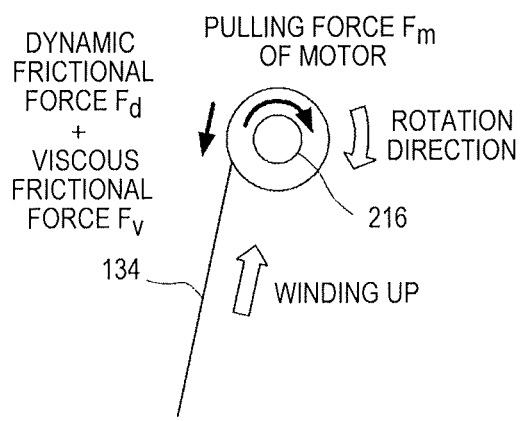
FIG. 7A is a diagram illustrating the relationship between the motion of the support wire and the frictional force in a swing phase.

FIG. 7A illustrates a situation where the support wire 134 is wound up by the winding-up mechanism, and this situation is observed in the swing phase. A frictional force acting when the support wire 134 is wound up by the winding-up mechanism at a speed v includes a dynamic frictional force $F_d$ and a viscous frictional force $F_v$ acting in a direction opposite to the winding-up direction, namely, acting in the unwinding direction. The dynamic frictional force $F_d$ is a constant frictional force that acts between the winding-up mechanism and the support wire 134, and the viscous frictional force $F_v$ is a frictional force that is generated in accordance with the movement of the support wire 134 and that is proportionate to the speed of the movement. At this time, the dynamic frictional force $F_d$ and the viscous frictional force $F_v$ act in a direction opposite to the direction of a pulling force $F_m$, generated by the motor (hereinafter, referred to as "pulling force $F_m$ of the motor" where appropriate). Therefore, the pulling force $F_m$ is adjusted to be increased by an amount corresponding to the sum of the dynamic frictional force $F_d$ and the viscous frictional force $F_v$, so as to bear the weight of the gait assist device 120.

Figure 7B:
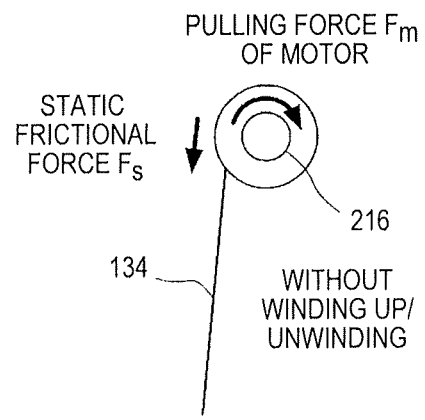
FIG. 7B is a diagram illustrating the relationship between the motion of the support wire and the frictional force at the time when the swing phase ends and an affected leg of the trainee is grounded, so that the affected leg is shifted to foot-grounding.

FIG. 7B illustrates a situation where the support wire 134 is neither wound up nor unwound, and this situation is observed at the time when the swing phase ends and the affected leg of the trainee 900 is grounded, so that the affected leg is shifted to foot-grounding. A frictional force acting at this time is a static frictional force $F_s$ that acts in the unwinding direction, which is the same as the direction of the dynamic frictional force acting immediately before foot-grounding. The static frictional force $F_s$ is a constant frictional force that acts between the winding-up mechanism and the support wire 134, and is larger than the dynamic frictional force $F_d$. This situation is also observed at the time when the swing phase starts from the foot-grounding.

Figure 7C:
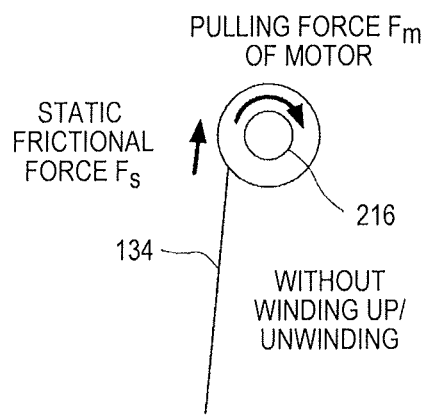
FIG. 7C is a diagram illustrating the relationship between the motion of the support wire and the frictional force at the time when the affected leg is shifted from the foot-grounding at which the affected leg is grounded to a stance phase in which the affected leg is moved backward by the action of a treadmill.

FIG. 7C illustrates a situation where the support wire 134 is neither wound up nor unwound, and this situation is observed at the time when the affected leg is shifted from the foot-grounding at which the affected leg is grounded to the stance phase in which the affected leg is moved backward by the action of the treadmill 131. A frictional force acting at this time is a static frictional force $F_s$ that acts in the winding-up direction. This situation is observed also at the time when the foot-grounding occurs immediately before the affected leg is shifted from the stance phase to the swing phase.

Figure 7D:
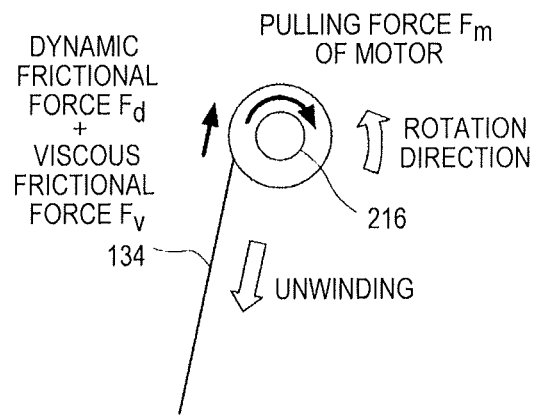
FIG. 7D is a diagram illustrating the relationship between the motion of the support wire and the frictional force in the stance phase.

FIG. 7D illustrates a situation where the support wire 134 is unwound from the winding-up mechanism, and this situation is observed in the stance phase. A frictional force acting at the time when the support wire 134 is unwound from the winding-up mechanism at a speed v includes a dynamic frictional force $F_d$ and a viscous frictional force $F_v$ that act in the winding-up direction. At this time, the dynamic frictional force $F_d$ and the viscous frictional force $F_v$ act in the same direction as the direction of a pulling force $F_m$ of the motor. Therefore, the pulling force $F_m$ is adjusted to be decreased by an amount corresponding to the sum of the dynamic frictional force $F_d$ and the viscous frictional force $F_v$, so as to bear the weight of the gait assist device 120.

The pulling force $F_m$ of the motor is preferably adjusted such that the dynamic frictional force $F_d$, the viscous frictional force $F_v$, and the static frictional force $F_s$ that act depending on the situations illustrated in FIGS. 7A to 7D are cancelled out and a certain part of the weight of the gait assist device 120 is always borne. In other words, the trainee 900 preferably receives a certain weight-bearing force regardless of the state of walking. However, when the affected leg is shifted from the swing phase to the stance phase, state changes occur in the order of FIG. 7A→7B→7C→7D within a short period of time. In addition, when the affected leg is shifted from the stance phase to the swing phase, state changes occur in the order of FIG. 7D→7C→7B→7A within a short period of time. That is, in state change including a situation where the affected leg is at a standstill for a moment and the support wire 134 is at a speed of zero at which the support wire 134 is neither wound up nor unwound, the frictional forces vary significantly and rapidly.

In the swing phase and the stance phase, the overall control unit 210 adjusts the pulling force $F_m$ of the motor in accordance with the speed of the support wire 134 while acquiring detection results from the ammeter 215 and the encoder 216, such that the dynamic frictional force $F_d$ and the viscous frictional force $F_v$ are cancelled out. However, if adjustment is performed in this manner when the speed of the support wire 134 is around zero, the frictional forces vary significantly and rapidly. Therefore, it is difficult to appropriately adjust the pulling force $F_m$, resulting in hunting, that is, a phenomenon in which a weight-bearing force significantly oscillates within a short period of time. In view of this, in a certain period of time including the time at which the speed of the support wire 134 is zero, the gait training apparatus 100 in the present embodiment gives a higher priority to reducing the occurrence of hunting even if the weight of the gait assist device 120 cannot be borne.

Figure 8:
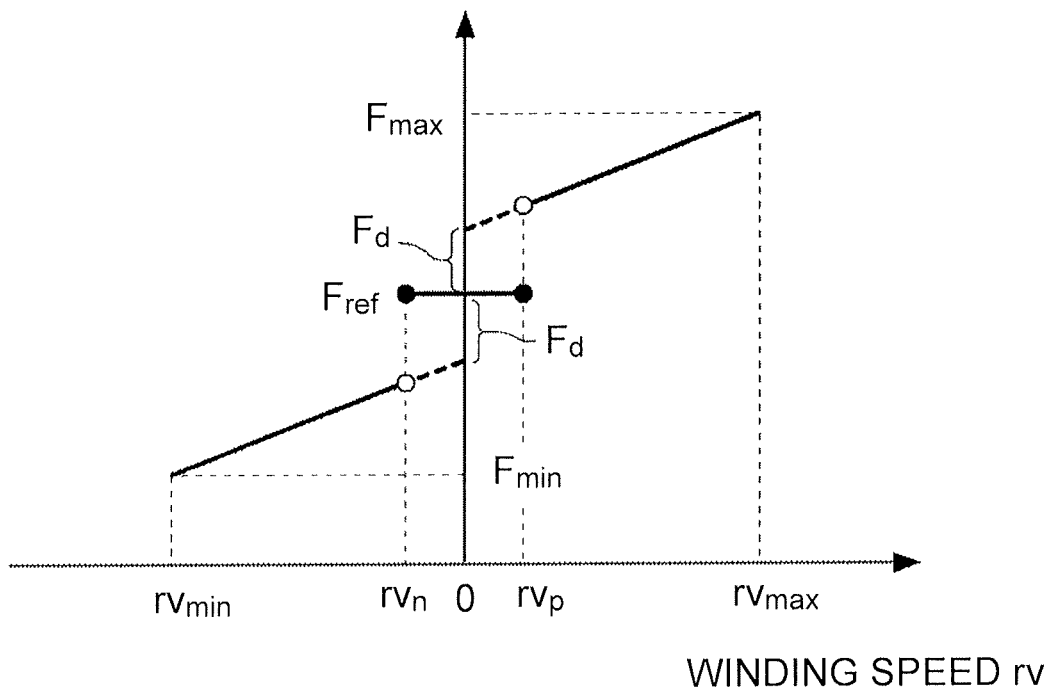
FIG. 8 is a graph illustrating the relationship between the winding speed and the pulling force generated by a motor.

Next, description will be provided on a concrete adjustment of the pulling force $F_m$ of the motor based on the winding speed of the support wire 134. FIG. 8 is a graph illustrating the relationship between the winding speed rv of the support wire 134 and the pulling force $F_m$ of the motor. The abscissa axis of the graph represents the winding speed rv, and the ordinate axis of the graph represents the pulling force $F_m$ of the motor.

When the winding speed rv takes a positive value, the winding-up mechanism is winding up the support wire 134. When the winding speed rv takes a negative value, the winding-up mechanism is unwinding the support wire 134. As described above with reference to FIG. 6, the maximum value of the winding speed is $rv_{max}$, and the minimum value of the winding speed is $rv_{min}$.

In the present embodiment, a range including a speed of zero $[rv_n, rv_p]$ ($rv_n < 0 < rv_p$) is defined. While the speed rv is within this range ($rv_n \leq rv \leq rv_p$), the pulling force $F_m$ of the motor is maintained at a certain value $F_{ref}$. That is, Equation (1) is satisfied.

$$F_m = F_{ref} (rv_n \leq rv \leq rv_p)$$ Equation (1)

$F_{ref}$ is a pulling force required to bear the weight of the gait assist device 120 in a stationary state where no frictional force is generated. Therefore, $F_{ref}$ is set in advance based on the weight of the gait assist device 120.

During the swing phase where the speed rv is within the range of $rv_p < rv \leq rv_{max}$, the pulling force $F_m$ of the motor is set to a value obtained by adding a value corresponding to the sum of the dynamic frictional force $F_d$ and the viscous frictional force $F_v$ to $F_{ref}$, based on the relationship illustrated in FIG. 7A. That is, Equation (2) is satisfied.

$$F_m = F_{ref} + (F_d + F_v)(rv_p < rv \leq rv_{max})$$ Equation (2)

Here, $F_v$ is proportionate to the speed rv. Therefore, when K denotes a proportionality coefficient, Equation (3) is satisfied.

$$F_m = F_{ref} + (F_d + K \cdot rv)(rv_p < rv \leq rv_{max})$$ Equation (3)

Note that $F_{max}$ satisfies $F_{max} = F_{ref} + (F_d + K \cdot rv_{max})$.

During the stance phase where the speed rv is within the range of $rv_{min} \leq rv < rv_n$, the pulling force $F_m$ of the motor is set to a value obtained by subtracting a value corresponding to the sum of the dynamic frictional force $F_d$ and the viscous frictional force $F_v$ from $F_{ref}$, based on the relationship illustrated in FIG. 7D. That is, Equation (4) is satisfied.

$$F_m = F_{ref} - (F_d + F_v)(rv_{min} \leq rv < rv_n)$$ Equation (4)

Here, $F_v$ is proportionate to the speed rv. Therefore, when K denotes a proportionality coefficient, Equation (5) is satisfied in consideration of the fact that the speed rv takes a negative value, $$F_m = F_{ref} - (F_d - K \cdot rv)(rv_{min} \leq rv < rv_n)$$ Equation (5)

Note that $F_{min}$ satisfies $F_{min} = F_{ref} - (F_d - K \cdot rv_{min})$.

Figure 9:
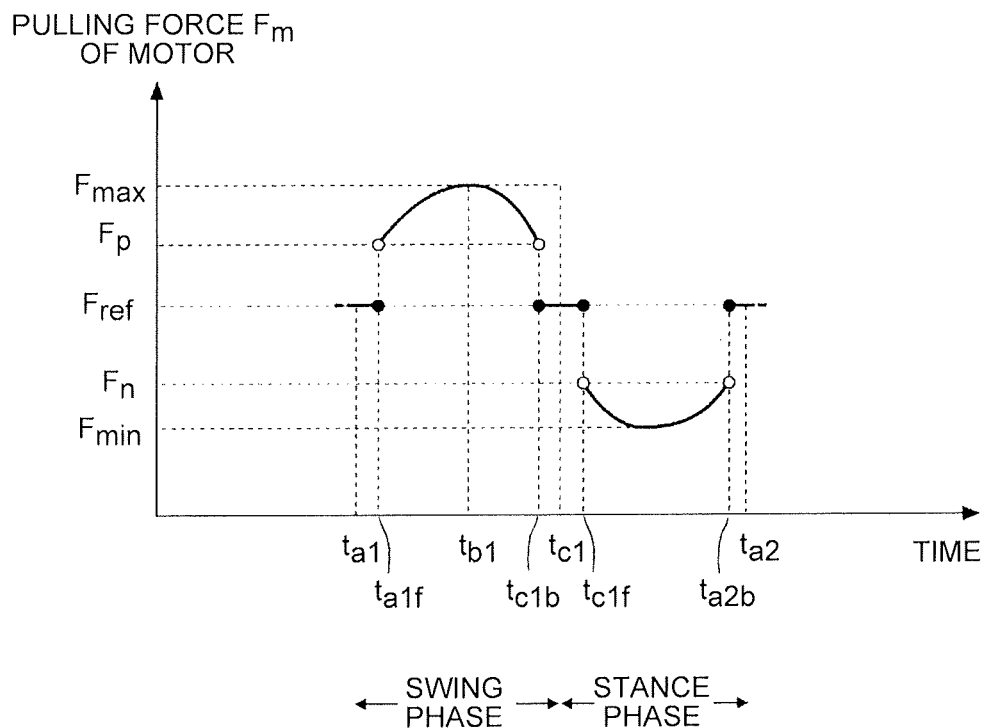
FIG. 9 is a graph illustrating the relationship between the leg movement of the trainee and the pulling force generated by the motor.

FIG. 9 is a graph illustrating the relationship between the leg movement of the trainee 900 and the pulling force of the motor. Specifically, FIG. 9 is obtained by applying the function indicated by FIG. 8 to the winding speed rv illustrated in FIG. 6 and making the ordinate axis represent the pulling force $F_m$. The abscissa axis of the graph represents the lapse of time, and the ordinate axis of the graph represents the pulling force $F_m$ applied to the support wire 134 by the motor.

At time $t_{a1}$, the affected leg enters the swing phase. However, $F_m$ is maintained at $F_{ref}$ which is a certain value, until the winding speed rv reaches $rv_p$ at time $t_{a1f}$. The winding speed rv then exceeds $rv_p$ at time $t_{a1f}$, reaches the maximum value $rv_{max}$ at time $t_{b1}$. Until the winding speed rv returns to $rv_p$ at time $t_{c1b}$, $F_m$ takes a value calculated by Equation (3). In the drawing, $F_p$ satisfies $F_p = F_{ref} + (F_d + K \cdot rv_p)$.

$F_m$ is maintained at $F_{ref}$ which is a certain value, during a period after the winding speed rv reaches $rv_p$ at time $t_{c1b}$ in the swing phase and until the winding speed rv reaches $rv_n$ at time $t_{c1f}$ in the stance phase, and the period includes time $t_{c1}$ at which the affected leg is grounded (at this time, rv=0). $F_m$ takes a value calculated by Equation (5) during a period after the winding speed rv falls below $rv_n$ at time $t_{c1f}$ and until the winding speed rv returns to $rv_n$ at time $t_{a2b}$, and the period includes a time at which the winding speed rv takes the minimum value $rv_{min}$. In the drawing, $F_m$ satisfies $F_m = F_{ref} - (F_d - K \cdot rv_n)$. $F_m$ is maintained at $F_{ref}$ which is a certain value, during a period after the winding speed rv reaches $rv_n$ at time $t_{a2b}$ in the stance phase and until time $t_{a2}$ at which the affected leg is shifted out of the stance phase (at this time, rv=0).

Figure 10:
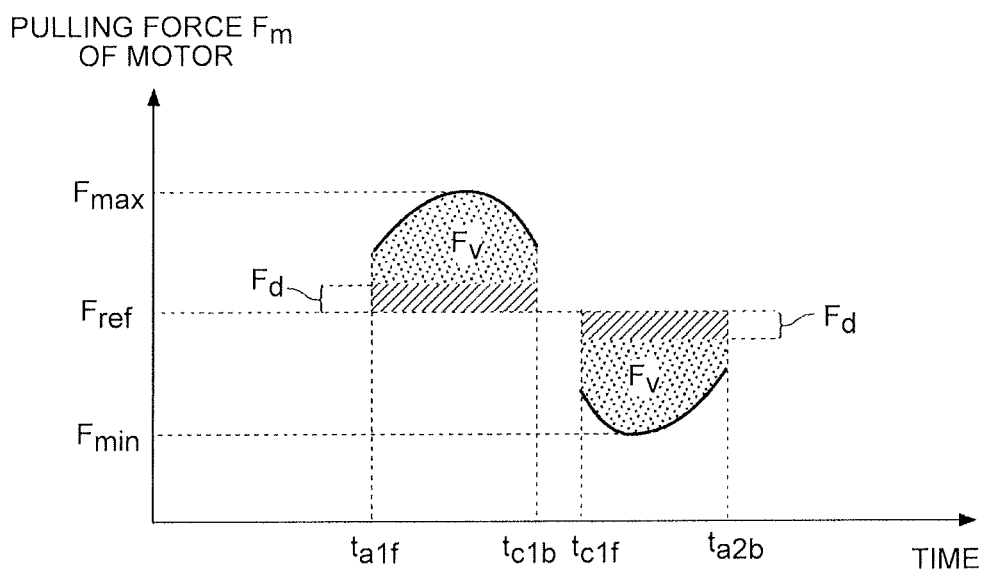
FIG. 10 is a graph illustrating the relationship between the pulling force generated by the motor and the frictional force.

FIG. 10 is a graph illustrating the relationship between the pulling force of the motor and the frictional force. Specifically, in FIG. 10, components that are attributable to frictional forces are illustrated for the pulling force $F_m$ of the motor illustrated in FIG. 9. As in FIG. 9, the abscissa axis of the graph represents the lapse of time, and the ordinate axis of the graph represents the pulling force $F_m$ applied to the support wire 134 by the motor.

During a period from time $t_{a1f}$ to time $t_{c1b}$ within the swing phase, the dynamic frictional force $F_d$ included in the pulling force $F_m$ of the motor and added to $F_{ref}$ takes a certain value at any time during this period. On the other hand, the viscous frictional force $F_v$ added to $F_{ref}$ is a variable value that varies from moment to moment with the lapse of time.

During a period from time $t_{c1f}$ to time $t_{a2b}$ within the stance phase, the dynamic frictional force $F_d$ included in the pulling force $F_m$ of the motor and subtracted from $F_{ref}$ takes a certain value at any time during this period. On the other hand, the viscous frictional force $F_v$ subtracted from $F_{ref}$ is a variable value that varies from moment to moment with the lapse of time.

Figure 11:
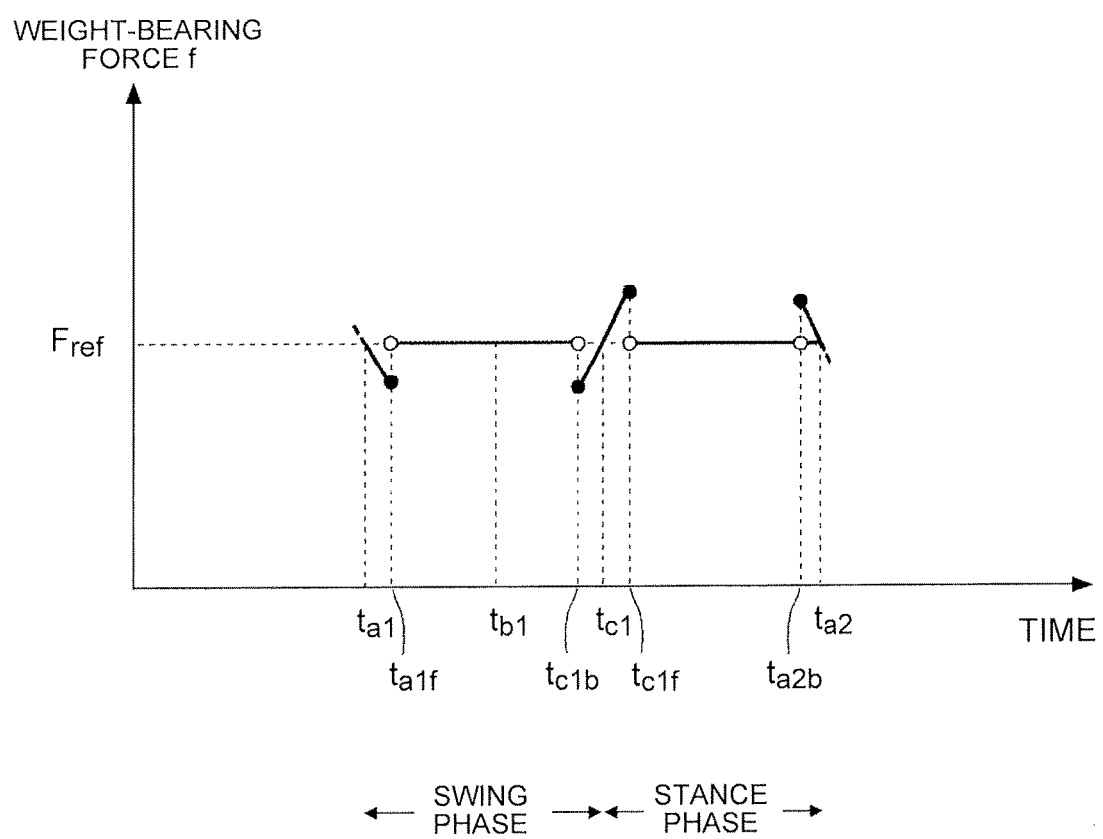
FIG. 11 is a graph illustrating the relationship between the leg movement of the trainee and the weight-bearing force.

FIG. 11 is a graph illustrating the relationship between the leg movement of the trainee 900 and the weight-bearing force that actually acts on the gait assist device 120. That is, FIG. 11 is a graph illustrating how the burden on the trainee 900 due to the weight of the gait assist device 120 is reduced when the motor applies the pulling force $F_m$ to the support wire 134, as illustrated in FIG. 9. The abscissa axis of the graph represents the lapse of time, and the ordinate axis of the graph represents the weight-bearing force f that represents reduction in the burden on the trainee 900 due to the weight of the gait assist device 120.

A period from time $t_{a1}$ to time $t_{a1f}$ within the swing phase is a period in which the pulling force of the motor is maintained at $F_{ref}$, which is a certain value, although the dynamic frictional force $F_d$ and the viscous frictional force $F_v$ are actually generated. Therefore, during this period, the weight-bearing force is slightly insufficient by an amount corresponding to the dynamic frictional force $F_d$ and the viscous frictional force $F_v$. During a period from time $t_{a1f}$ to time $t_{c1b}$ within the swing phase, the pulling force of the motor is adjusted in consideration of the dynamic frictional force $F_d$ and the viscous frictional force $F_v$. Therefore, $F_{ref}$ that bears the weight of the gait assist device 120 is stably maintained.

A period from time $t_{c1b}$ to time $t_{c1f}$ is a transient period in which the affected leg is shifted from the swing phase to the stance phase. In this period, the pulling force of the motor is maintained at $F_{ref}$, which is a certain value, although the static frictional force $F_s$ is actually generated, or the dynamic frictional force $F_d$ and the viscous frictional force $F_v$ are actually generated. Therefore, during this period, the weight-bearing force is slightly insufficient by an amount corresponding to the static frictional force $F_s$, or by an amount corresponding to the dynamic frictional force $F_d$ and the viscous frictional force $F_v$. More specifically, a difference between $F_s$ and $F_d$ may cause further variations in the weight-bearing force but the variations are caused within a considerably short period of time and are not illustrated in the drawing. In addition, the variations caused in such a short period of time are not recognized by the trainee 900, and the influence of the variations can be actually ignored. A phenomenon similar to that described above may occur within a period from time $t_{a1}$ to time $t_{a1f}$ and a period from time $t_{a2b}$ to time $t_{a2}$, but this phenomenon can be ignored as well.

During a period from time $t_{c1f}$ to time $t_{a2b}$ within the stance phase, the pulling force of the motor is adjusted in consideration of the dynamic frictional force $F_d$ and the viscous frictional force $F_v$. Therefore, $F_{ref}$ that bears the weight of the gait assist device 120 is stably maintained. A period from time $t_{a2b}$ to time $t_{a2}$ within the stance phase is a period in which the pulling force of the motor is maintained at $F_{ref}$, which is a certain value, although the dynamic frictional force $F_d$ and the viscous frictional force $F_v$ are actually generated. Therefore, during this period, the weight-bearing force is slightly excessive by an amount corresponding to the dynamic frictional force $F_d$ and the viscous frictional force $F_v$.

Figure 12:
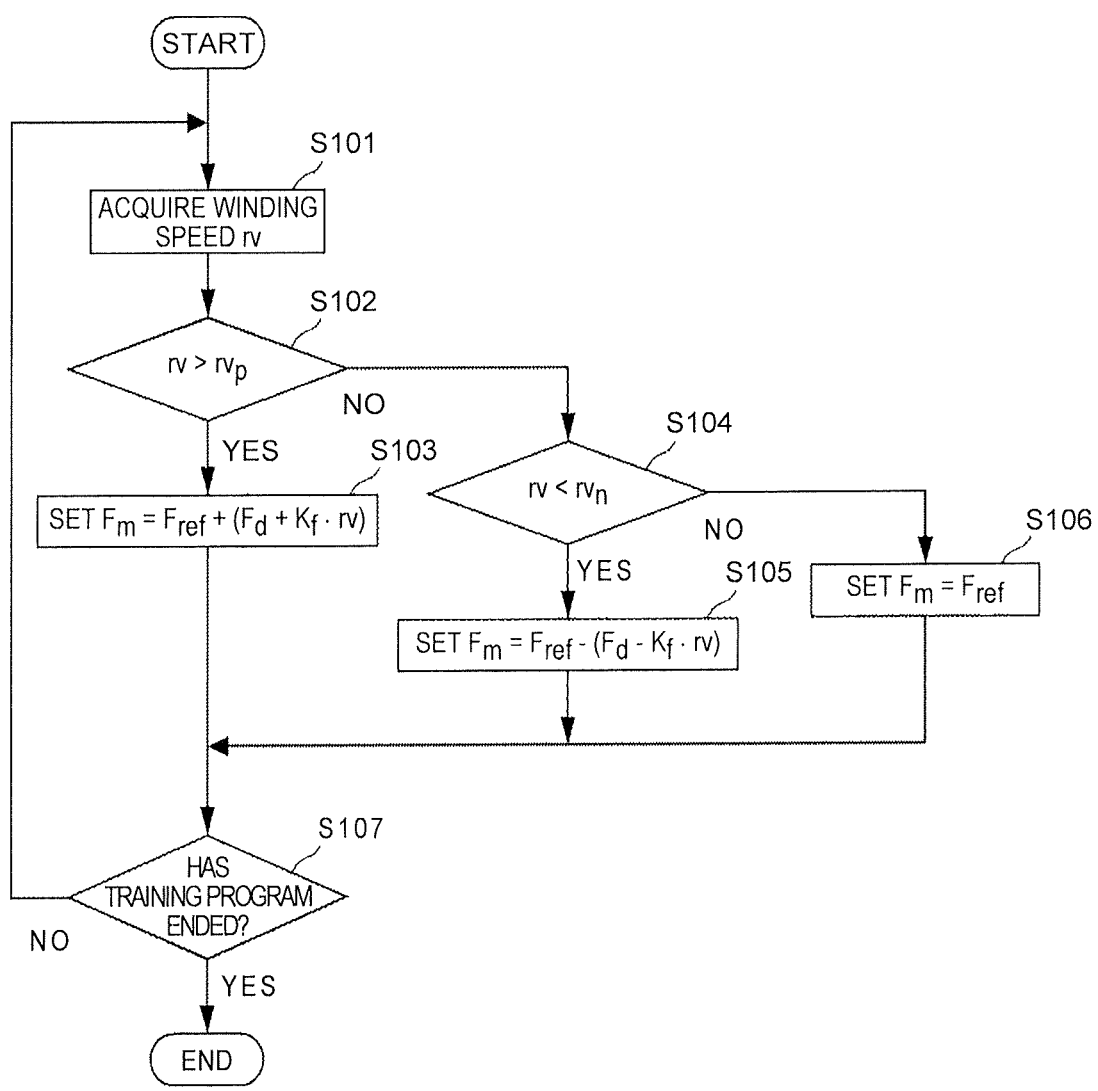
FIG. 12 illustrates a flowchart of a load reduction process.

FIG. 12 illustrates a flowchart of a load reduction process. The flowchart is started when the operation of the gait assist device 120 is started.

In step S101, the overall control unit 210 acquires a detection signal from the encoder 216 to acquire a winding speed rv of the support wire 134. Then, the overall control unit 210 proceeds to step S102, and determines in step S102 whether the acquired winding speed rv is higher than a predetermined value $rv_p$. When the overall control unit 210 determines that the acquired winding speed rv is higher than the predetermined value $rv_p$, the overall control unit 210 proceeds to step S103, whereas when the overall control unit 210 makes a negative determination, the overall control unit 210 proceeds to step S104.

In step S103, the overall control unit 210 sets a pulling force $F_m$ to be applied to the support wire 134 by the motor, to a value obtained by Equation (3) described above. Then, in order to achieve a current value at which a pulling force having the set value is generated, the overall control unit 210 transmits a drive signal corresponding to the current value to the pulling driving unit 214 while monitoring a detected value from the ammeter 215.

When the overall control unit 210 proceeds to step S104, the overall control unit 210 determines whether the acquired winding speed rv is lower than a predetermined value $rv_n$. When the overall control unit 210 determines that the acquired winding speed rv is lower than the predetermined value $rv_n$, the overall control unit 210 proceeds to step S105, and when the overall control unit 210 makes a negative determination, the overall control unit 210 proceeds to step S106.

In step S105, the overall control unit 210 sets the pulling force $F_m$ to be applied to the support wire 134 by the motor, to a value obtained by Equation (5) described above. Then, in order to achieve a current value at which a pulling force having the set value is generated, the overall control unit 210 transmits a drive signal corresponding to the current value to the pulling driving unit 214 while monitoring a detected value from the ammeter 215. In step S106, the overall control unit 210 sets the pulling force $F_m$ to be applied to the support wire 134 by the motor, to a value obtained by Equation (1) described above. Then, in order to achieve a current value at which a pulling force having the set value is generated, the overall control unit 210 transmits a drive signal corresponding to the current value to the pulling driving unit 214 while monitoring a detected value from the ammeter 215.

When a process in step S103, step S105, or step S106 is completed, the overall control unit 210 proceeds to step S107 to determine whether a training program has ended. When the overall control unit 210 determines that the training program has not ended, the overall control unit 210 returns to step S101. When the overall control unit 210 determines that the training program has ended, the overall control unit 210 ends the series of processes.

The foregoing description is provided on the case where the affected leg is moved relatively smoothly, by way of example. However, some trainee 900 who are carrying out the gait training will not always make a smooth transition between the states illustrated in FIG. 4 along the arrowed dotted lines, and there may be cases where the leg movement is non-smooth, such as a case where the affected leg stops while being lifted. Next, such a case will be described.

Figure 13:
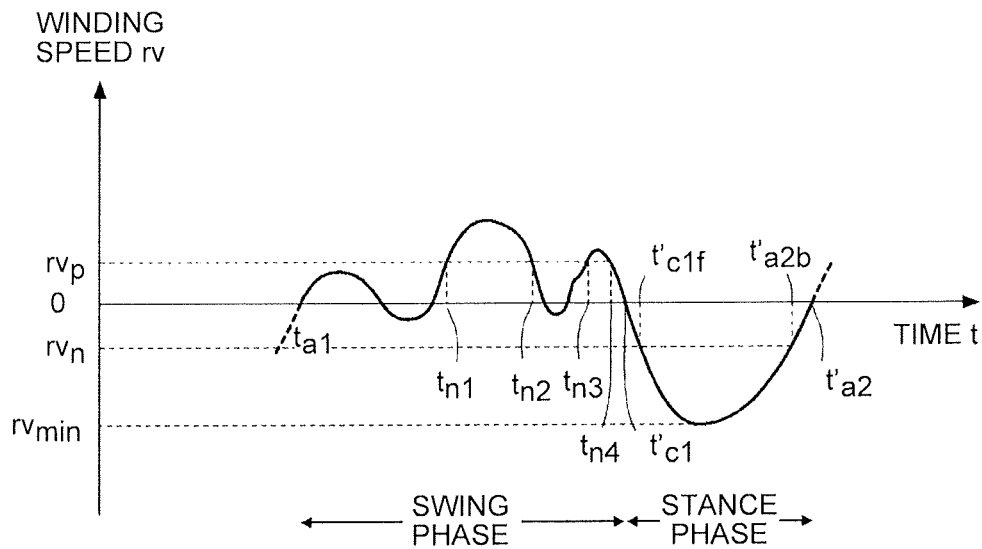
FIG. 13 is a graph illustrating the relationship between the non-smooth leg movement and the winding speed of the support wire.

FIG. 13 is a graph illustrating the relationship between an example of a trainee 900's non-smooth leg movement and the winding speed of the support wire 134. As in FIG. 6, the abscissa axis of the graph represents the lapse of time, and the ordinate axis of the graph represents the winding speed rv at which the winding-up mechanism winds up the support wire 134.

The trainee 900 lifts the affected leg at time $t_{a1}$, so that the affected leg enters a swing phase. However, the movement of the affected leg is sluggish and unstable, and the winding speed rv does not exceed $rv_p$, which is a threshold value, until time $t_{n1}$. A period from time $t_{a1}$ to time $t_{n1}$ includes a moment at which the winding speed rv becomes zero. Although rv exceeds $rv_p$ at time $t_{n1}$, the winding speed rv slows down and falls below $rv_p$ at time $t_{n2}$, and exceeds $rv_p$ again at time $t_{n3}$. Then, immediately before the end of the swing phase, the winding speed rv falls below $rv_p$ at time $t_{n4}$. A period from time $t'_{c1}$ to time $t'_{a2}$, including times $t'_{c1f}$, $t'_{a2b}$ is a stance phase in which the affected leg is automatically moved backward by action of the treadmill 131. Therefore, the situation in this period is the same as the situation within the period from time $t_{c1}$ to time $t_{a2}$ in FIG. 6.

As described above, there may be a case where the leg movement is unstable and the winding speed rv becomes zero in the swing phase. Even in such a case, it is important to apply the function indicated in FIG. 8 to adjust the pulling force $F_m$ of the motor so as to prevent the occurrence of hunting, that is, a phenomenon in which a weight-bearing force significantly oscillates within a short period of time, in the swing phase.

Figure 14:
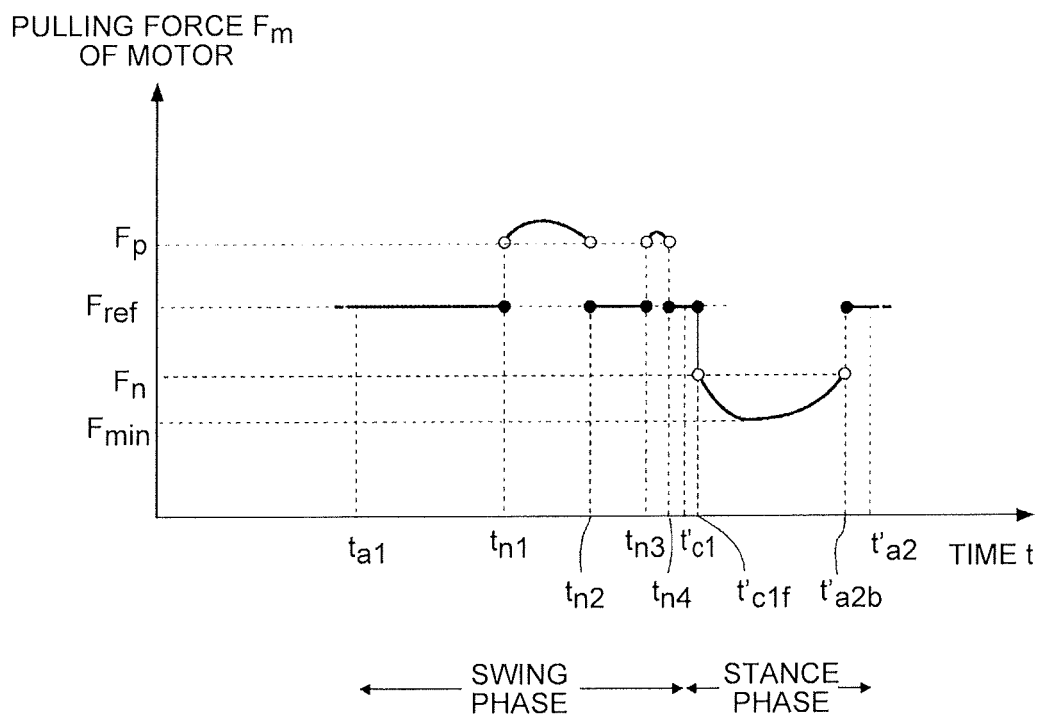
FIG. 14 is a graph illustrating the relationship between the non-smooth leg movement and the pulling force generated by the motor.

Description will be provided on the pulling force of the motor in a case where the function indicated in FIG. 8 is applied to the leg movement illustrated in FIG. 13. FIG. 14 is a graph illustrating the relationship between the leg movement illustrated in FIG. 13 and the pulling force of the motor. Specifically, FIG. 14 is obtained by applying the function indicated in FIG. 8 to the winding speed rv illustrated in FIG. 13 and making the ordinate axis represent the pulling force $F_m$. The abscissa axis of the graph represents the lapse of time, and the ordinate axis of the graph represents the pulling force $F_m$ applied to the support wire 134 by the motor.

Although detailed description will not be provided, the overall control unit 210 adjusts the pulling force $F_m$ to $F_{ref}$, which is a certain value, or adjusts the pulling force $F_m$ to a variable value in consideration of the dynamic frictional force $F_d$ and the viscous frictional force $F_v$, depending on the periods in FIG. 13. Such variations in the pulling force $F_m$ are caused by the process in the flowchart illustrated in FIG. 12. Even when the leg movement is unstable, rapid and significant variations that may cause hunting are not generated in the pulling force $F_m$. Therefore, it is possible to relatively stably reduce the burden on the trainee 900.

In the embodiment described above, the pulling force $F_m$ of the motor is set to the certain value $F_{ref}$ when the winding speed rv is within the prescribed range of $[rv_n, rv_p]$, including a speed of zero. However, the pulling force $F_m$ during this period may be set in accordance with another rule. In this period, if the pulling force $F_m$ is set based on the winding speed rv, there is a high possibility that hunting will occur. Therefore, the pulling force $F_m$ may be set so as to be independent of rv.

Figure 15:
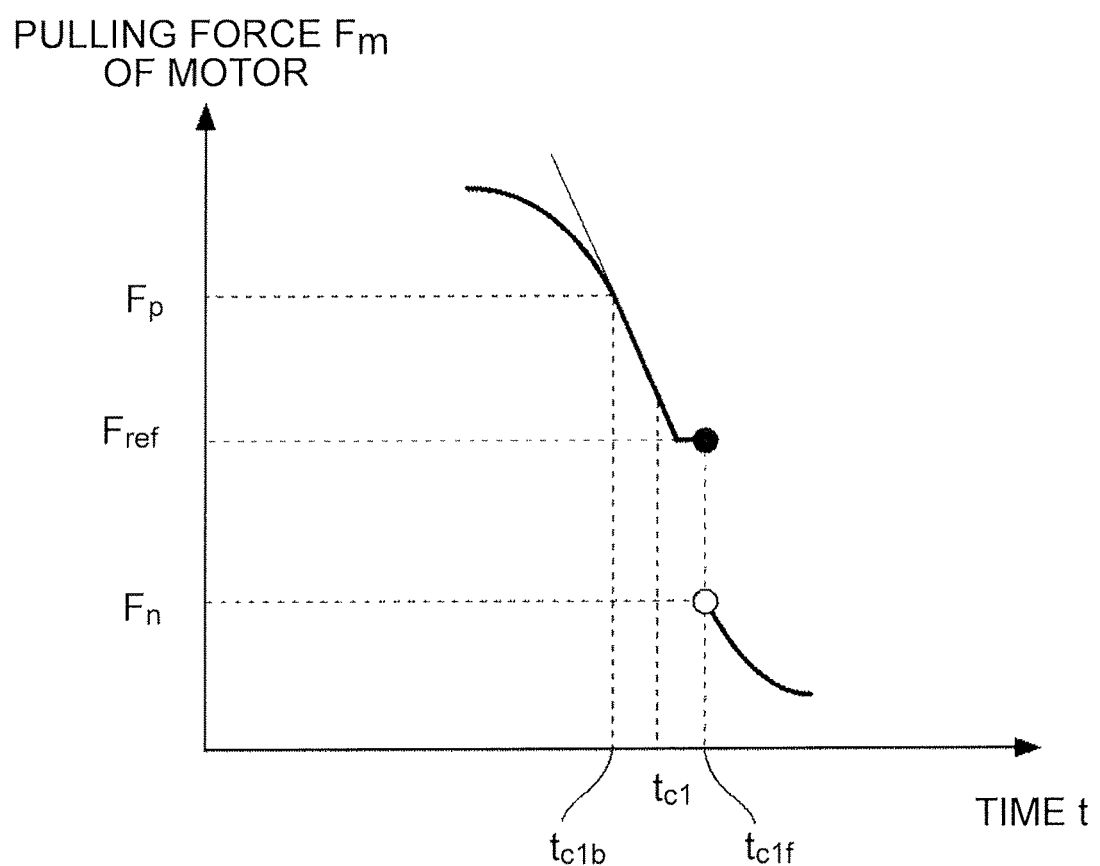
FIG. 15 is a graph illustrating the relationship between the leg movement and the pulling force generated by the motor in another example.

FIG. 15 is a graph illustrating the relationship between the leg movement and the pulling force of the motor in another setting example in which the pulling force $F_m$ is independent of the winding speed rv. FIG. 15 is an enlarged view of a range from time $t_{c1b}$ to time $t_{c1f}$ and its vicinity in FIG. 9.

When rv falls below the threshold value $rv_p$ at time $t_{c1b}$, the pulling force is set to $F_{ref}$ in the example illustrated in FIG. 9. However, in the present modified example, the pulling force is not set to a discontinuous value, and the inclination of a tangent, at time $t_{c1b}$, to a curve of the pulling force $F_m$ up to time $t_{c1b}$ is calculated. From time $t_{c1b}$, the pulling force $F_m$ is represented by a straight line having the inclination. Based on the straight line set in this manner, the pulling force $F_m$ is not discontinuous at time $t_{c1b}$, so that the trainee 900 is less likely to recognize variations in the weight-bearing force.

If $F_m$ calculated based on the straight line set in this manner becomes equal to $F_{ref}$, $F_m$ may be set to $F_{ref}$, which is a certain value, during a period after $F_m$ becomes equal to $F_{ref}$ and until rv falls out of the prescribed range of $[rv_n, rv_p]$. When $F_m$ is set in this manner, the range of variations in the pulling force $F_m$ is the same regardless of whether rv exceeds $rv_p$ or falls below $rv_n$ next time. Therefore, the trainee 900 does not recognize larger variations in the weight-bearing force. The setting that makes the pulling force $F_m$ independent of the winding speed rv may be a setting that makes the pulling force $F_m$ continuous based on a function other than a straight line and using the elapsed time as a variable, or may be a setting that makes $F_m$ a certain value other than $F_{ref}$.

In the embodiment described above, the range including a speed of zero is defined for the winding speed rv. The overall control unit 210 controls the motor such that a predetermined pulling force that is independent of the speed is obtained when the detected winding speed falls within the prescribed range, whereas the overall control unit 210 controls the motor such that a pulling force calculated based on the speed is obtained when the detected winding speed falls out of the prescribed range. When the motor is controlled in this way, even if the movement of the leg is unstable, the pulling force can be adjusted as appropriate, as described above with reference to FIG. 13 and FIG. 14.

In related art, hunting having greater influence occurs at the time when the moving direction of the support wire 134 is reversed. The time when the moving direction of the support wire 134 is reversed is included in a period in which the affected leg is shifted from the swing phase to the stance phase and a period in which the affected leg is shifted from the stance phase to the swing phase. In view of this, a state detecting unit configured to detect a grounding state of the affected leg of the trainee 900 may be provided. When the overall control unit 210 determines based on the results of detection that the affected leg is shifted from the swing phase to the stance phase or shifted from the stance phase to the swing phase, the overall control unit 210 may control the motor such that a predetermined pulling force that is independent of the speed is obtained. On the other hand, when the overall control unit 210 determines that the affected leg is maintained in the swing phase or in the stance phase, the overall control unit 210 may control the motor such that a pulling force calculated based on the speed is obtained.

Figure 16:
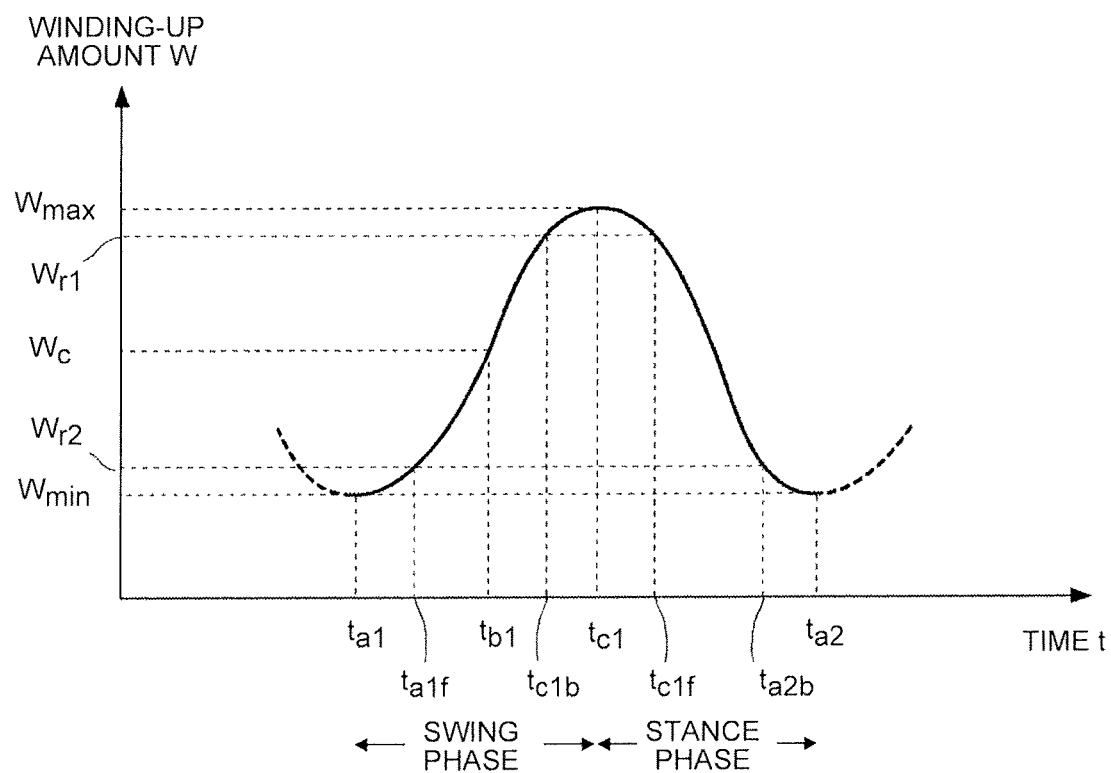
FIG. 16 is a graph illustrating the relationship between a change in the leg movement and the winding-up amount of the support wire.

FIG. 16 is a graph illustrating the relationship between a change in the leg movement and the winding-up amount of the support wire 134. FIG. 16 is made by providing additional information to FIG. 5. The abscissa axis of the graph represents the lapse of time, and the ordinate of the graph represents the winding-up amount of the support wire 134, that is, the amount by which the support wire 134 is wound up by the winding mechanism.

As described above, the affected leg is shifted from the stance phase to the swing phase at time $t_{a1}$ at which the winding-up amount W reaches the minimum value $W_{min}$. The affected leg is shifted from the swing phase to the stance phase at time $t_{c1}$ at which the winding-up amount W reaches the maximum value $W_{max}$. Therefore, the encoder 216 can be used as the state detecting unit configured to detect a grounding state of the affected leg. That is, $W_{r2}$ close to the minimum value $W_{min}$ is used as a threshold value, and the overall control unit 210 determines that the affected leg is shifted from the stance phase to the swing phase when the winding-up amount W is within a range of [$W_{min}$, $W_{r2}$]. $W_{r1}$ close to the maximum value $W_{max}$ is used as a threshold value, and the overall control unit 210 determines that the affected leg is shifted from the swing phase to the stance phase when the winding-up amount W is within a range of [$W_{r1}$, $W_{max}$]. The overall control unit 210 determines that the affected leg is maintained in the swing phase or in the stance phase when the winding-up amount W is within a range of ($W_{r2}$, $W_{r1}$).

If a determination can be made in the above-described manner, the pulling force $F_m$ of the motor is set to $F_{ref}$ which is a certain value, for example, when the winding-up amount W is within one of the range [$W_{min}$, $W_{r2}$] and the range [$W_{r1}$, $W_{max}$]. Alternatively, another setting method may be employed as described above. When the winding-up amount W is within the range [$W_{min}$, $W_{r2}$], the winding speed rv at this time is acquired, and the pulling force $F_m$ of the motor is set based on the value of the winding speed rv by Equation (6) or (7).

$$F_m = F_{ref} + (F_d + K \cdot rv)(0 < rv \leq rv_{max}) \quad \text{Equation (6)}$$

$$F_m = F_{ref}(F_d - K \cdot rv)(rv_{min} \leq rv < 0) \quad \text{Equation (7)}$$

The sole sensor 125 provided in the sole frame 124 may be used as the state detecting unit configured to detect a grounding state of the affected leg. As described above, the sole sensor 125 can detect the magnitude and the distribution of a vertical load received by the sole of the trainee 900. Therefore, the overall control unit 210 can determine a period in which a certain variation occurs in the distribution of load to be a period in which the affected leg is shifted from the swing phase to the stance phase or the affected leg is shifted from the stance phase to the swing phase, and can determine a period in which no variation occurs in the distribution of load to be a period in which the affected leg is maintained in the swing phase or in the stance phase.

If a determination can be made in the above-described manner, as in the above-described control executed based on the winding-up amount W, the pulling force $F_m$ of the motor is set to $F_{ref}$ which is a certain value, during a period in which a certain variation occurs in the distribution of load, and the pulling force $F_m$ of the motor is set according to Equation (6), (7) during a period in which no variation occurs in the distribution of load. This configuration can also produce advantageous effects similar to those produced by the above-described configuration.

The present embodiment described above has the configuration in which one support pulling unit 135 is disposed in front of an area over the head of the trainee 900, and the gait assist device 120 is pulled by one support wire 134. However, a plurality of support wires may be disposed to pull the gait assist device 120. As a modified example of the present embodiment, description will be provided on a configuration in which the gait assist device 120 is pulled by two support wires.

Figure 17:
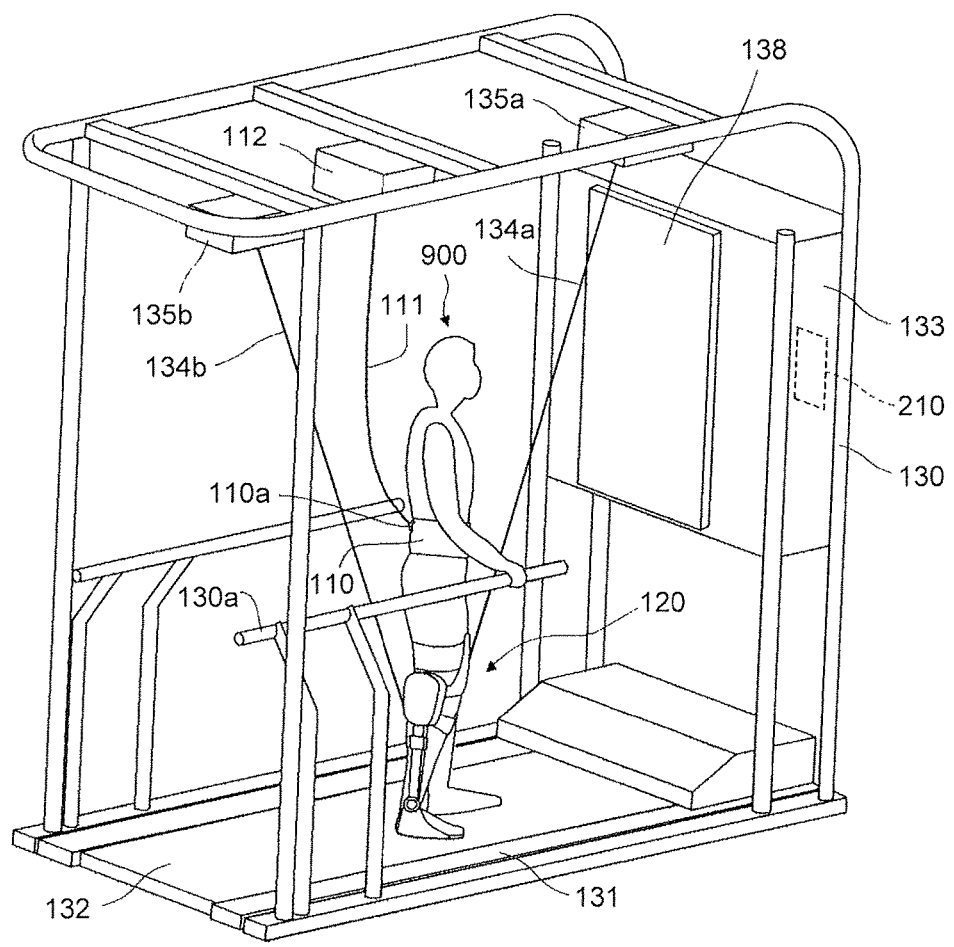
FIG. 17 is a schematic perspective view of a gait training apparatus according to a modified example of the embodiment.

FIG. 17 is a schematic perspective view of a gait training apparatus 100' according to the modified example of the present embodiment. A frame 130 of the gait training apparatus 100' supports a support pulling unit 135a in the vicinity of an area above and ahead of the head of the trainee 900, and supports a support pulling unit 135b in the vicinity of an area above and behind the head of the trainee 900. The support wire 134a is coupled at one end to a winding-up mechanism of the support pulling unit 135a, and is coupled at the other end to the gait assist device 120. The support wire 134b is coupled at one end to a winding-up mechanism of the support pulling unit 135b, and is coupled at the other end to the gait assist device 120. The configuration of each of the support pulling units 135a, 135b is the same as that of the support pulling unit 135 of the gait training apparatus 100, and a pulling driving unit 214 includes, for example, motors for pulling the support wires 134a, 134b, respectively, and driving circuits for the motors. Other elements of the configuration are substantially the same as those of the gait training apparatus 100, and description thereof will be omitted.

Figure 18:
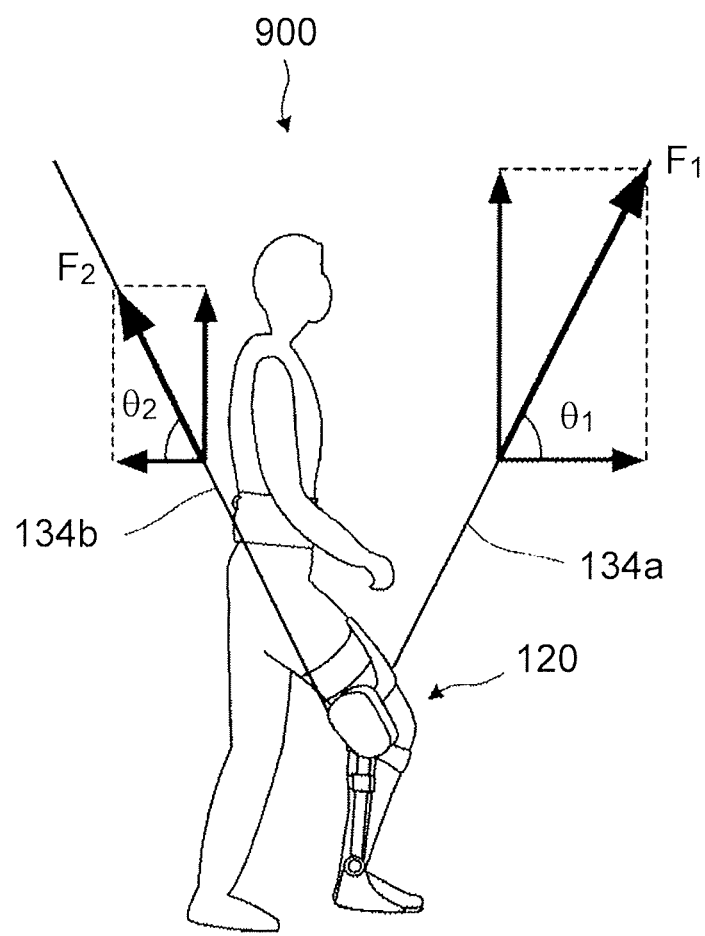
FIG. 18 is a diagram illustrating how to share a weight-bearing force.

FIG. 18 is a diagram for illustrating how to share a weight-bearing force. As illustrated in FIG. 18, a pulling force of the motor that pulls the support wire 134a is denoted by $F_1$, and a pulling force of the motor that pulls the support wire 134b is denoted by $F_2$. An angle formed between the support wire 134a and the horizontal direction is denoted by $\theta_1$, and an angle formed between the support wire 134b and the horizontal direction is denoted by $\theta_2$. In this case, $F_c$ that is a force for pulling up the gait assist device 120 is expressed as follows.

$$F_c = F_1 \sin \theta_1 + F_2 \sin \theta_2 \quad \text{Equation (8)}$$

It is assumed here that variations in the angles $\theta_1$, $\theta_2$ due to the leg movement are considerably small and can be ignored.

In this case, $F_c$ may be set to be equal to $F_{ref}$ in a stationary state in which no frictional force acts. When $F_c$ is set, the pulling forces to be respectively borne by the support wires 134a, 134b can be determined because the angles $\theta_1$, $\theta_2$ are constant. Here, attention is focused on thrust force generated in the front-back direction.

As illustrated in FIG. 12, when pulling forces are applied to the support wires 134a, 134b, a thrust force is generated in the front-back direction. When the thrust force is denoted by $F_h$, Equation (9) is satisfied.

$$F_h = F_1 \cos \theta_1 - F_2 \cos \theta_2 \quad \text{Equation (9)}$$

Assistance to the trainee 900 by the driving force $F_h$ serves a part of the function of the gait assist device 120, and is set based on the balance between the state of the trainee 900, the performance of the gait assist device 120, and so forth. Therefore, when $F_h$ is set, a ratio between $F_1$ and $F_2$ can be determined because the angles $\theta_1$, $\theta_2$ are constant. That is, the output ratio between the motors for pulling the support wires 134a, 134b can be determined.

Based on the ratio, the pulling forces borne by the support wires 134a, 134b, respectively, in the stationary state in which no frictional force acts are determined. That is, $F_{1ref}$ and $F_{2ref}$ that satisfy Equation (10) can be determined.

$$F_{ref} = F_{1ref} \sin \theta_1 + F_{2ref} \sin \theta_2 \quad \text{Equation (10)}$$

When $F_{1ref}$ and $F_{2ref}$ are determined, $F_{1ref}$ and $F_{2ref}$ may be substituted for $F_{ref}$ in the function indicated in FIG. 8, and the function may be corrected so as to compensate for the dynamic frictional force $F_d$ and the viscous frictional force $F_v$. Based on the function determined in this manner, the overall control unit 210 may control the pulling forces $F_1$, $F_2$ of the motors that pull the support wires 134a, 134b, respectively.

The foregoing description has been provided on the assumption that the angles $\theta_1$, $\theta_2$ are constant for the sake of convenience. However, when the angles $\theta_1$, $\theta_2$ vary, the output ratio between the motors that pull the support wires may be determined based on the angles $\theta_1$, $\theta_2$ at each time. The pulling forces that are borne by the support wires in order to bear the weight of the gait assist device 120 may be set in advance, and a thrust force generated in the front-back direction may be cancelled out by adjusting the output of the motor of the gait assist device 120.

In the foregoing embodiment and the foregoing modified example, the affected leg to which the gait assist device 120 is fitted is indirectly pulled by the support wire coupled to the gait assist device. However, the support wire may be wound directly around the affected leg and pulled, without coupling the support wire to the gait assist device.

What is claimed is:

1. A gait training apparatus including a gait assist device fitted to a leg of a trainee and configured to assist a movement of the leg of the trainee, the gait training apparatus comprising:
   a wire configured to directly or indirectly pull the leg fitted with the gait assist device from a position above the trainee's head;
   a motor configured to apply a pulling force to the wire;
   a control unit configured to control the motor to adjust the pulling force;
   a housing mechanism configured to retract or release the wire in response to a motion of the leg; and
   a speed detecting unit configured to detect a speed at which the housing mechanism retracts or releases the wire, wherein
   the control unit is configured to control the motor such that the pulling force is adjusted to a predetermined pulling force that is independent of the speed, when the speed is within a prescribed range defined in advance and including zero, and
   the control unit is configured to control the motor such that the pulling force is adjusted to a pulling force calculated based on the speed, when the speed is out of the prescribed range.

2. The gait training apparatus according to claim 1, wherein, when the control unit calculates the pulling force based on the speed, the pulling force is calculated to be increased or decreased by an amount corresponding to a viscous frictional force that is proportionate to the speed and that is generated in the housing mechanism.

3. The gait training apparatus according to claim 1, wherein:
   the housing mechanism includes a winding shaft configured to wind the wire; and
   the speed detecting unit is configured to detect a rotation speed of the winding shaft, as the speed.

4. The gait training apparatus according to claim 1, wherein the housing mechanism is disposed at a position above the trainee's head and ahead of an area on which the leg of the trainee is expected to be grounded.

5. The gait training apparatus according to claim 1, further comprising two pulling units each including the wire, the motor, the housing mechanism, and the speed detecting unit, wherein
   a first pulling unit that is one of the pulling units is disposed at a position above the trainee's head and ahead of the trainee,
   a second pulling unit that is the other one of the pulling units is disposed above the trainee's head and backward of the trainee, and
   the control unit is configured to control the motor of the first pulling unit and the motor of the second pulling unit.

6. The gait training apparatus according to claim 5, wherein the control unit is configured to adjust an output ratio between the motor of the first pulling unit and the motor of the second pulling unit so as to assist a leg movement of the leg.

7. A gait training apparatus including a gait assist device fitted to a leg of a trainee and configured to assist a movement of the leg of the trainee, the gait training apparatus comprising:
   a wire configured to directly or indirectly pull the leg fitted with the gait assist device from a position above the trainee's head;
   a motor configured to apply a pulling force to the wire;
   a control unit configured to control the motor to adjust the pulling force;
   a housing mechanism configured to retract or release the wire in response to a motion of the leg;
   a speed detecting unit configured to detect a speed at which the housing mechanism retracts or releases the wire; and
   a state detecting unit configured to detect a grounding state of the leg of the trainee, wherein,
   the control unit is configured to control the motor such that the pulling force is adjusted to a predetermined pulling force that is independent of the speed, when the control unit determines, based on a result of detection by the state detecting unit, that the leg is shifted from a swing phase to a stance phase or that the leg is shifted from the stance phase to the swing phase, and
   the control unit is configured to control the motor such that the pulling force is adjusted to a pulling force that is calculated based on the speed, when the control unit determines, based on a result of detection by the state detecting unit, that the leg is maintained in the swing phase or maintained in the stance phase.

8. The gait training apparatus according to claim 7, wherein the state detecting unit includes a pressure sensor provided in a sole portion in the gait assist device, the sole portion being a portion on which the trainee's sole is placed.

9. The gait training apparatus according to claim 7, wherein the state detecting unit includes a retracted amount detecting unit configured to detect a retracted amount that is an amount of the wire retracted in the housing mechanism.

10. The gait training apparatus according to claim 7, wherein, when the control unit calculates the pulling force based on the speed, the pulling force is calculated to be increased or decreased by an amount corresponding to a viscous frictional force that is proportionate to the speed and that is generated in the housing mechanism.

11. The gait training apparatus according to claim 7, wherein:
   the housing mechanism includes a winding shaft configured to wind the wire; and
   the speed detecting unit is configured to detect a rotation speed of the winding shaft, as the speed.

12. The gait training apparatus according to claim 7, wherein the housing mechanism is disposed at a position above the trainee's head and ahead of an area on which the leg of the trainee is expected to be grounded.

13. The gait training apparatus according to claim 7, further comprising two pulling units each including the wire, the motor, the housing mechanism, and the speed detecting unit, wherein
   a first pulling unit that is one of the pulling units is disposed at a position above the trainee's head and ahead of the trainee,
   a second pulling unit that is the other one of the pulling units is disposed above the trainee's head and backward of the trainee, and
   the control unit is configured to control the motor of the first pulling unit and the motor of the second pulling unit.

14. The gait training apparatus according to claim 13, wherein the control unit is configured to adjust an output ratio between the motor of the first pulling unit and the motor of the second pulling unit so as to assist a leg movement of the leg.

\* \* \* \* \*

UNITED STATES PATENT AND TRADEMARK OFFICE
CERTIFICATE OF CORRECTION

PATENT NO. : 10,449,107 B2
APPLICATION NO. : 15/833102
DATED : October 22, 2019
INVENTOR(S) : Tomoe Maekita et al.

It is certified that error appears in the above-identified patent and that said Letters Patent is hereby corrected as shown below:

On the Title Page

Item (71), the Applicant's name is incorrect. Item (71) should read:
-- (71) Applicant: TOYOTA JIDOSHA KABUSHIKI KAISHA, Toyota-shi (JP) --

Signed and Sealed this
Eleventh Day of February, 2020

Andrei Iancu
*Director of the United States Patent and Trademark Office*